(12) United States Patent
Park et al.

(10) Patent No.: US 12,076,169 B2
(45) Date of Patent: Sep. 3, 2024

(54) METHOD AND DEVICE FOR MEASURING BIOMETRIC INFORMATION IN ELECTRONIC DEVICE

(71) Applicant: SAMSUNG ELECTRONICS CO., LTD., Suwon-si (KR)

(72) Inventors: Jongin Park, Suwon-si (KR); Hwan Shim, Suwon-si (KR); Hongji Lee, Suwon-si (KR); Taehan Jeon, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 957 days.

(21) Appl. No.: 17/040,709

(22) PCT Filed: Apr. 5, 2019

(86) PCT No.: PCT/KR2019/004098
§ 371 (c)(1),
(2) Date: Sep. 23, 2020

(87) PCT Pub. No.: WO2019/194651
PCT Pub. Date: Oct. 10, 2019

(65) Prior Publication Data
US 2021/0012130 A1 Jan. 14, 2021

(30) Foreign Application Priority Data

Apr. 6, 2018 (KR) .................. 10-2018-0040198

(51) Int. Cl.
*A61B 5/00* (2006.01)
*G06F 18/25* (2023.01)
(Continued)

(52) U.S. Cl.
CPC ............ *A61B 5/744* (2013.01); *A61B 5/7271* (2013.01); *G06F 18/251* (2023.01); *G06V 40/10* (2022.01); *G06V 40/11* (2022.01); *G06V 40/50* (2022.01)

(58) Field of Classification Search
CPC ..... A61B 5/744; A61B 5/7271; A61B 5/0077; A61B 5/02108; A61B 5/14532;
(Continued)

(56) References Cited

U.S. PATENT DOCUMENTS 10,599,904 B2 * 3/2020 Kwon .................. G06V 40/28
10,872,220 B2 * 12/2020 Cho .................. G06V 40/1318
(Continued)

FOREIGN PATENT DOCUMENTS

| JP | 2006-167269 | 6/2006 |
|---|---|---|
| JP | 2014-087484 | 5/2014 |

(Continued)

OTHER PUBLICATIONS

Office Action dated Aug. 30, 2022 in Korean Application No. 10-2018-0040198 and English-language machine translation.
(Continued)

*Primary Examiner* — Bobbak Safaipour
(74) *Attorney, Agent, or Firm* — Nixon & Vanderhye, P.C.

(57) ABSTRACT

Disclosed in various embodiments of the present invention are a method and a device for measuring a user's biometric information in an electronic device and providing information related to the biometric information. An electronic device according to various embodiments of the present invention comprises a sensor module, a camera module, a display device, and a processor, wherein the processor can be configured to: execute an application; acquire a user's first biometric information on the basis of the sensor module
(Continued)

while the operation relating to the application is performed; estimate a user's health information at least one the basis of the first biometric information, and link the health information with the operation relating to the application so as to display same through the display device. Various embodiments are possible.

14 Claims, 19 Drawing Sheets

(51) Int. Cl.
*G06V 40/10* (2022.01)
*G06V 40/50* (2022.01)

(58) Field of Classification Search
CPC ... A61B 5/165; A61B 5/6843; A61B 5/02416; A61B 5/02438; A61B 5/0245; A61B 5/14551; A61B 5/6898; A61B 5/1116; A61B 5/7275; G06F 18/251; G06V 40/10; G06V 40/11; G06V 40/50; H04M 1/725; H04M 1/724; H04M 2201/34; H04M 2201/38; H04M 2250/12
See application file for complete search history.

(56) References Cited

U.S. PATENT DOCUMENTS

| | | | |
|---|---|---|---|
| 11,559,211 B2 * | 1/2023 | Jeong | A61B 5/14517 |
| 2005/0215919 A1 | 9/2005 | Kim et al. | |
| 2007/0021676 A1 | 1/2007 | Han et al. | |
| 2009/0157429 A1 * | 6/2009 | Lee | A61B 5/0205 705/3 |
| 2014/0121544 A1 | 5/2014 | Sugo et al. | |
| 2016/0065840 A1 * | 3/2016 | Kim | A61B 5/6898 348/207.99 |
| 2016/0142407 A1 * | 5/2016 | Chun | H04L 63/0861 726/5 |
| 2017/0032168 A1 * | 2/2017 | Kim | H04L 63/0861 |
| 2017/0119307 A1 * | 5/2017 | Shim | A61B 5/0022 |
| 2017/0238875 A1 | 8/2017 | Olivier et al. | |
| 2017/0255812 A1 * | 9/2017 | Kwon | G06V 40/13 |
| 2017/0265079 A1 * | 9/2017 | Kim | H04W 12/065 |
| 2017/0319123 A1 | 11/2017 | Voss et al. | |
| 2017/0323285 A1 | 11/2017 | Xing | |

FOREIGN PATENT DOCUMENTS

| | | |
|---|---|---|
| KR | 10-2006-0044520 | 5/2006 |
| KR | 10-2007-0011685 | 1/2007 |
| KR | 10-0869242 | 11/2008 |
| KR | 10-2016-0028093 | 3/2016 |
| KR | 10-2017-0143477 | 12/2017 |

OTHER PUBLICATIONS

International Search Report for PCT/KR2019/004098 dated Jul. 11, 2019, 11 pages.

Written Opinion of the ISA for PCT/KR2019/004098 dated Jul. 11, 2019, 6 pages.

* cited by examiner

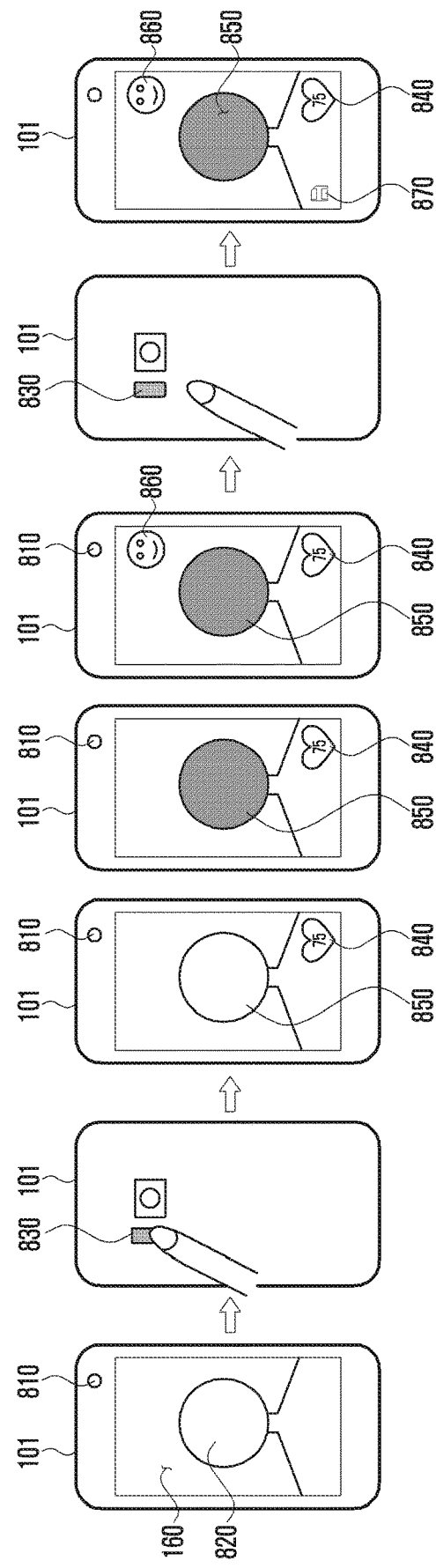

METHOD AND DEVICE FOR MEASURING BIOMETRIC INFORMATION IN ELECTRONIC DEVICE

CROSS-REFERENCE TO RELATED APPLICATIONS

This application is the U.S. national phase of International Application No. PCT/KR2019/004098 filed Apr. 5, 2019 which designated the U.S. and claims priority to Korean Application No. 10-2018-0040198 filed Apr. 6, 2018, the entire contents of each of which are hereby incorporated by reference.

BACKGROUND

The disclosure relates to a method and an apparatus for measuring biometric information of a user through an electronic device and providing information related to the biometric information.

DESCRIPTION OF RELATED ART

With the development of digital technology, various types of electronic devices, such as mobile communication terminals, smartphones, tablet personal computers (PCs), notebooks, personal digital assistants (PDAs), wearable devices, or digital cameras, have come to be widely used.

Recently, various services (or functions) for a user's health care have come to be provided through electronic devices. For example, the electronic device may acquire biometric information related to a user's health care, provide various pieces of health information (for example, heart rate information, blood sugar information, and stress information) to a user on the basis of the acquired biometric information, and may provide exercise coaching according to the biometric information.

SUMMARY

Measurement of biometric information through an electronic device may require a series of operations to be consciously performed by a user. For example, the user may be required to perform an operation (or action) of executing an application capable of measuring biometric information in the electronic device, preparing to measure the biometric information (for example, take a ready for biometric recognition through a sensor related to biometric information to be measured), and maintaining a fixed position for continuous measurement for a minimum measurement time configured for acquiring the corresponding biometric information. It is troublesome for the user to perform the series of operations for measuring the biometric information, which impedes the function of measuring biometric information using the electronic device and decreases the usability of associated applications. Further, 9.200 the electronic device individually measures pieces of biometric information and respective measurement results are provided for each piece of biometric information, the user is inconvenienced by a waiting time corresponding to the repeated performance of the measurement operation for the time required to obtain each piece of biometric information. For example, even for various pieces of biometric information measured using the same sensor at the same position of the body of the user, biometric information which can be estimated may vary depending on the measurement time, and thus the electronic device individually measure each piece of biometric information.

Various embodiments disclose a method and an apparatus for measuring at least one piece of biometric information without conscious effort by the user and are related to measurement of biometric information by the electronic device in a general environment in which the electronic device is used (or a general user experience).

Various embodiments disclose a method and an apparatus for estimating biometric information by merging discontinuous measurement data related to at least one piece of biometric information obtained in the general environment in which the electronic device is used.

Various embodiments disclose a method and an apparatus for monitoring whether biometric information is acquired while processing operations related to an application when the electronic device executes the application, collecting measurable biometric information on the basis of the monitoring result, associating the biometric information with the application through post-processing of the collected biometric information, and providing the same to the user.

In accordance with an aspect of the disclosure, an electronic device is provided. The electronic device includes: a sensor module; a camera module; a display; and a processor, wherein the processor is configured to execute an application, acquire first biometric information of a user, based on the sensor module while an operation related to the application is performed, estimate health information of the user, based on at least the first biometric information, and associate the health information with the operation related to the application and display the health information through the display device.

In accordance with another aspect of the disclosure, a method of operating an electronic device is provided. The method includes: executing an application; acquiring first biometric information of a user, based on a sensor module while an operation related to the application is performed; estimating health information of the user, based on at least the first biometric information; and associating the health information with the operation related to the application and displaying the health information through the display device.

In order to solve the technical problem, various embodiments of the disclosure may include a computer-readable recording medium having a program recorded therein in order to perform the method by a processor.

According to an electronic device and a method of operating the same according to various embodiments, it is possible to naturally measure a user's biometric information through implicit authentication that does not need a user's conscious effort or needs little conscious effort when the user executes an application. For example, the electronic device may measure biometric information without a user's conscious effort (or through implicit authentication) during a general user experience (for example, during a selfie, a voice call, or a video call) on the basis of a time and a situation suitable for user biometric sensing.

According to various embodiments, in implicit authentication, it is possible to induce the user to reduce the amount of time required for measurement by merging the results of discontinuous measurement. According to various embodiments, in providing biometric information provided over a time in which the user's biometric information is sensed, the biometric information may be provided as intuitive information by adding virtual-reality data to general user-experience information through an augmented-reality scheme for expressing virtual-reality data in real time. According to various embodiments, it is possible to reduce the incidence of failure associated with the need to continually measure biometric information by allowing temporal division of biometric information measurement, and to increase the frequency and availability (or usability) of acquisition of the user's biometric information by the user in everyday life.

BRIEF DESCRIPTION OF THE DRAWINGS

FIGS. 8A, 8B, 8C, 8D, 8E, 8F, and 8G illustrate an example in which an electronic device estimates health information according to various embodiments;

DETAILED DESCRIPTION

Figure 1:
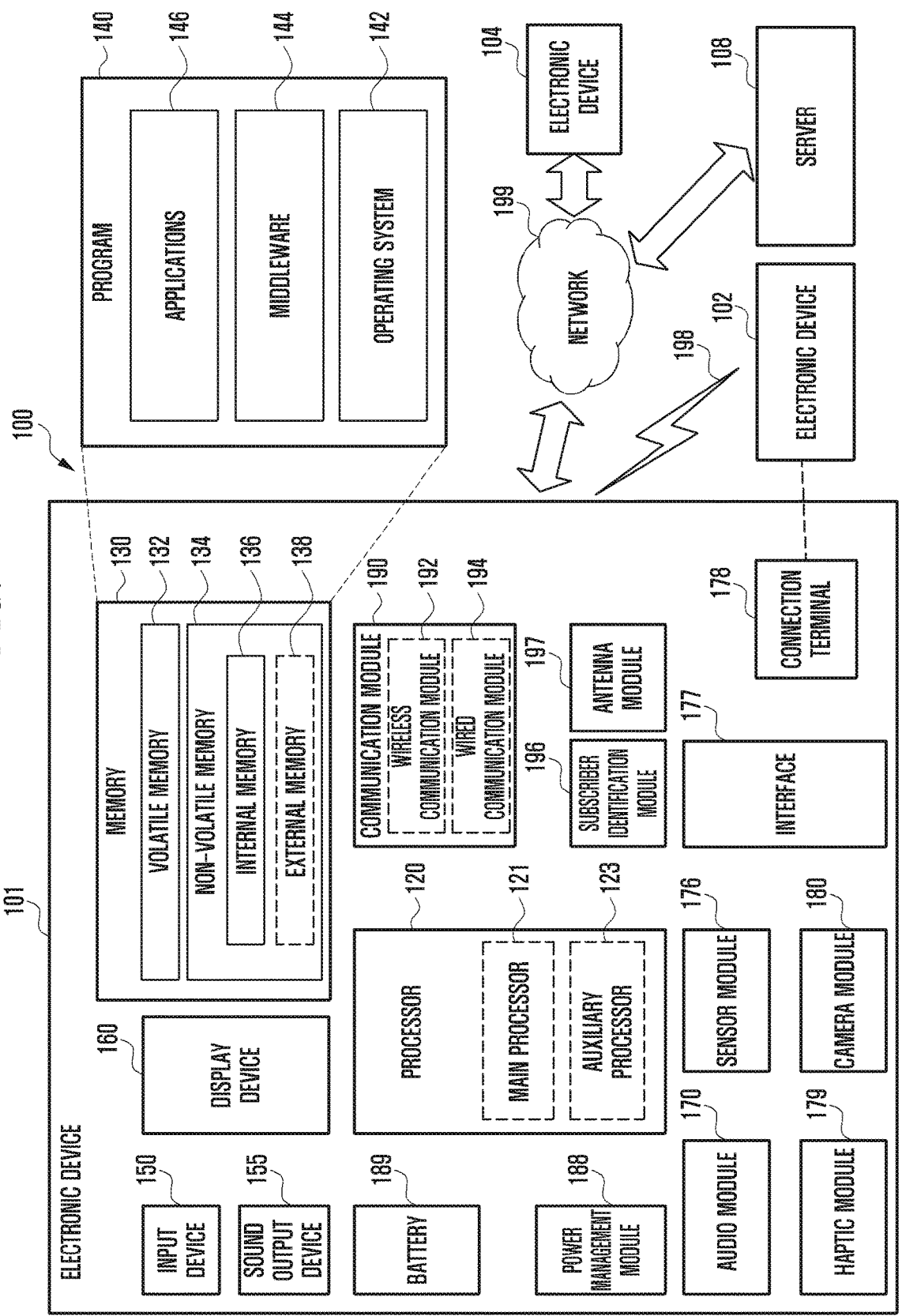
FIG. 1 illustrates an electronic device in a network environment according to an embodiment.

FIG. 1 illustrates an electronic device 101 in a network environment 100 according to an embodiment.

Referring to FIG. 1, the electronic device 101 in the network environment 100 may communicate with an electronic device 102 via a first network 198 (e.g., a short-range wireless communication network), with an electronic device 104 or a server 108 via a second network 199 (e.g., a long-range wireless communication network), or with the electronic device 104 via the server 108, and may include a processor 120, a memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) card 196, and an antenna module 197. At least one (e.g., the display device 160 or the camera module 180) of the components may be omitted from the electronic device 101, or one or more other components may be added in the electronic device 101. Some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. The processor 120 may load a command or data received from another component (e.g., the sensor module 176 or the communication module 190) in the volatile memory 132, process the command or the data stored in the volatile memory 132, and store resulting data in non-volatile memory 134. The processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). The auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101 and may include software (e.g., the program 140) and input data or output data for a command related thereto. The memory 130 may include the volatile memory 132 or the non-volatile memory 134.

The program 140 may be stored in the memory 130 as software, and may include an operating system (OS) 142, middleware 144, or an application 146.

The input device 150 may receive a command or data to be used by another component (e.g., the processor 120) of the electronic device 101, from the outside (e.g., a user) of the electronic device 101, and may include a microphone, a mouse, a keyboard, or a digital pen (e.g., a stylus pen).

The sound output device 155 may output sound signals to the outside of the electronic device 101 and may include a speaker or a receiver. The speaker may be used for general purposes, such as playing multimedia or playing record, and the receiver may be used for incoming calls and may be implemented as separate from, or as part of the speaker.

The display device 160 may visually provide information to the outside (e.g., a user) of the electronic device 101 and may include a display, a hologram device, or a projector and control circuitry to control a corresponding one of the display, hologram device, and projector. The display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa, and may obtain the sound via the input device 150, or output the sound via the sound output device 155 or a headphone of an external electronic device (e.g., an electronic device 102) directly (e.g., over wires) or wirelessly coupled with the electronic device 101.

The sensor module 176 may detect an operational state (e.g., power or temperature) of the electronic device 101 or an environmental state (e.g., a state of a user) external to the electronic device 101, and generate an electrical signal or data value corresponding to the detected state, and may include a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., over wires) or wirelessly, and may include a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102), and may include a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation, and may include a motor, a piezoelectric element, or an electric stimulator.

The camera module 180 may capture a still image or moving images and may include one or more lenses, image sensors, image signal processors, or flashes.

The power management module 188 may manage power supplied to the electronic device 101, and may be implemented as at least part of a power management integrated circuit (PMIC).

The battery 189 may supply power to at least one component of the electronic device 101, and may include a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. The communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., a LAN or a wide area network (WAN)). These various types of communication modules may be implemented as a single component (e.g., a single chip), or may be implemented as multi components (e.g., multi chips) separate from each other.

The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101 and may include an antenna including a radiating element composed of a conductive material or a conductive pattern formed in or on a substrate (e.g., a PCB). The antenna module 197 may include a plurality of antennas. In such a case, at least one antenna appropriate for a communication scheme used in the communication network, such as the first network 198 or the second network 199, may be selected by the communication module 190 (e.g., the wireless communication module 192) from the plurality of antennas. The signal or the power may then be transmitted or received between the communication module 190 and the external electronic device via the selected at least one antenna. Another component (e.g., an RFIC) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

Commands or data may be transmitted or received between the electronic device 101 and the external electronic device 104 via the server 108 coupled with the second network 199. Each of the electronic devices 102 and 104 may be a device of a same type as, or a different type, from the electronic device 101.

All or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing, as at least part of a reply to the request. To that end, a cloud, distributed, or client-server computing technology may be used, for example.

Figure 2:
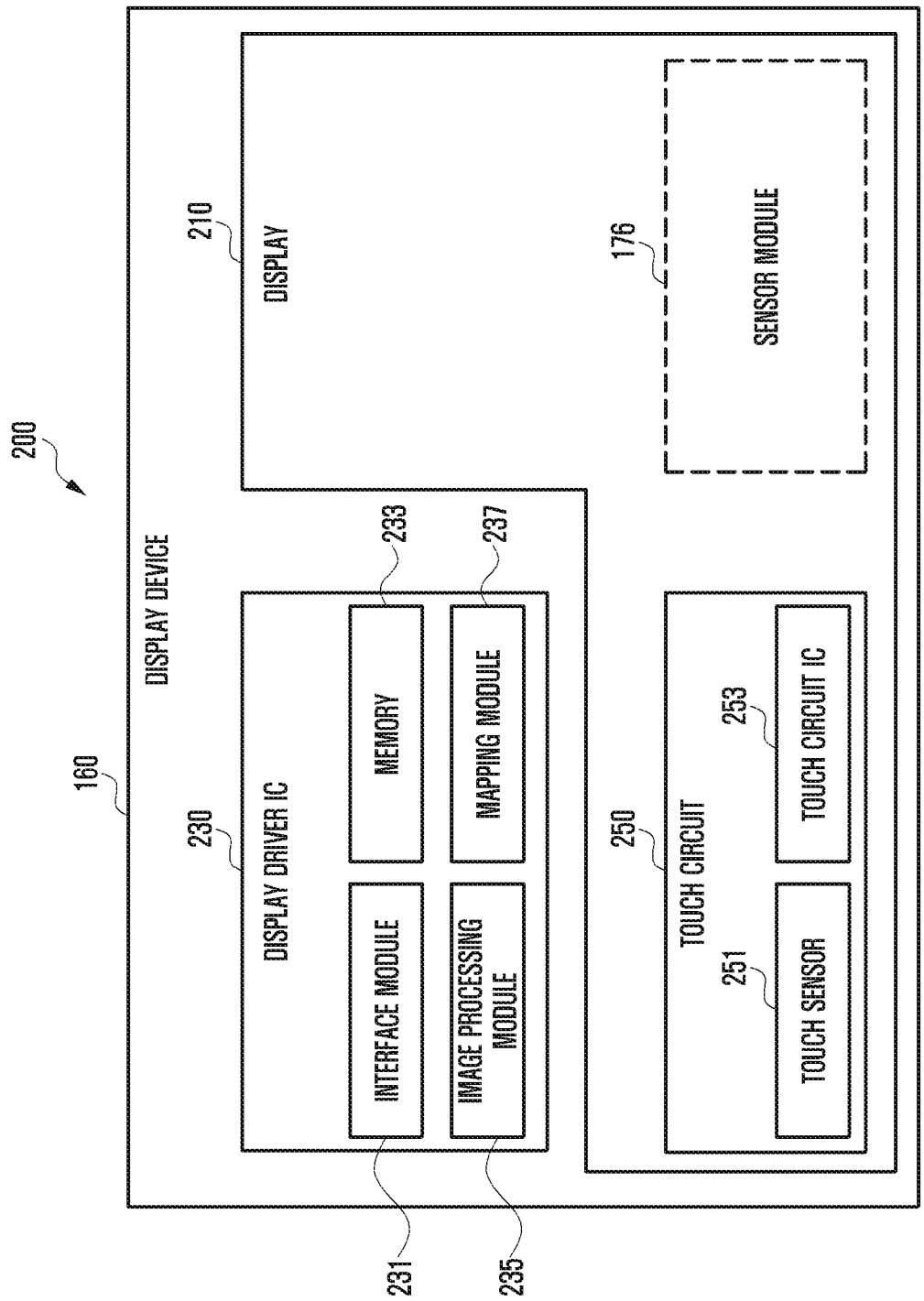
FIG. 2 is a block diagram illustrating the display device according to various embodiments.

FIG. 2 is a block diagram 200 illustrating the display device 160 according to various embodiments.

Referring to FIG. 2, the display device 160 may include a display 210 and a display driver integrated circuit (DDI) 230 to control the display 210. The DDI 230 may include an interface module 231, memory 233 (e.g., buffer memory), an image processing module 235, or a mapping module 237.

The DDI 230 may receive image information that contains image data or an image control signal corresponding to a command to control the image data from another component of the electronic device 101 via the interface module 231. For example, according to an embodiment, the image information may be received from the processor 120 (e.g., the main processor 121 (e.g., an application processor)) or the auxiliary processor 123 (e.g., a graphics processing unit) operated independently from the function of the main processor 121. The DDI 230 may communicate, for example, with touch circuitry 350 or the sensor module 176 via the interface module 231. The DDI 230 may also store at least part of the received image information in the memory 233, for example, on a frame by frame basis.

The image processing module 235 may perform pre-processing or post-processing (e.g., adjustment of resolution, brightness, or size) with respect to at least part of the image data. According to an embodiment, the pre-processing or post-processing may be performed, for example, based at least in part on one or more characteristics of the image data or one or more characteristics of the display 210.

The mapping module 237 may generate a voltage value or a current value corresponding to the image data pre-processed or post-processed by the image processing module 235. According to an embodiment, the generating of the voltage value or current value may be performed, for example, based at least in part on one or more attributes of the pixels (e.g., an array, such as an RGB stripe or a pentile structure, of the pixels, or the size of each subpixel). At least some pixels of the display 210 may be driven, for example, based at least in part on the voltage value or the current value such that visual information (e.g., a text, an image, or an icon) corresponding to the image data may be displayed via the display 210.

According to an embodiment, the display device 160 may further include the touch circuitry 250. The touch circuitry 250 may include a touch sensor 251 and a touch sensor IC 253 to control the touch sensor 251. The touch sensor IC 253 may control the touch sensor 251 to sense a touch input or a hovering input with respect to a certain position on the display 210. To achieve this, for example, the touch sensor 251 may detect (e.g., measure) a change in a signal (e.g., a voltage, a quantity of light, a resistance, or a quantity of one or more electric charges) corresponding to the certain position on the display 210. The touch circuitry 250 may provide input information (e.g., a position, an area, a pressure, or a time) indicative of the touch input or the hovering input detected via the touch sensor 251 to the processor 120. According to an embodiment, at least part (e.g., the touch sensor IC 253) of the touch circuitry 250 may be formed as part of the display 210 or the DDI 230, or as part of another component (e.g., the auxiliary processor 123) disposed outside the display device 160.

According to an embodiment, the display device 160 may further include at least one sensor (e.g., a fingerprint sensor, an iris sensor, a pressure sensor, or an illuminance sensor) of the sensor module 176 or a control circuit for the at least one sensor. In such a case, the at least one sensor or the control circuit for the at least one sensor may be embedded in one portion of a component (e.g., the display 210, the DDI 230, or the touch circuitry 250)) of the display device 160. For example, when the sensor module 176 embedded in the display device 160 includes a biometric sensor (e.g., a fingerprint sensor), the biometric sensor may obtain biometric information (e.g., a fingerprint image) corresponding to a touch input received via a portion of the display 210. As another example, when the sensor module 176 embedded in the display device 160 includes a pressure sensor, the pressure sensor may obtain pressure information corresponding to a touch input received via a partial or whole area of the display 210. According to an embodiment, the touch sensor 251 or the sensor module 176 may be disposed between pixels in a pixel layer of the display 210, or over or under the pixel layer.

The electronic device 101 according to embodiments may be one of various types of electronic devices, such as a portable communication device (e.g., a smartphone), a computer device, a portable multimedia device, a portable medical device, a camera, a wearable device, or a home appliance. However, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise.

As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., over wires), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 3:
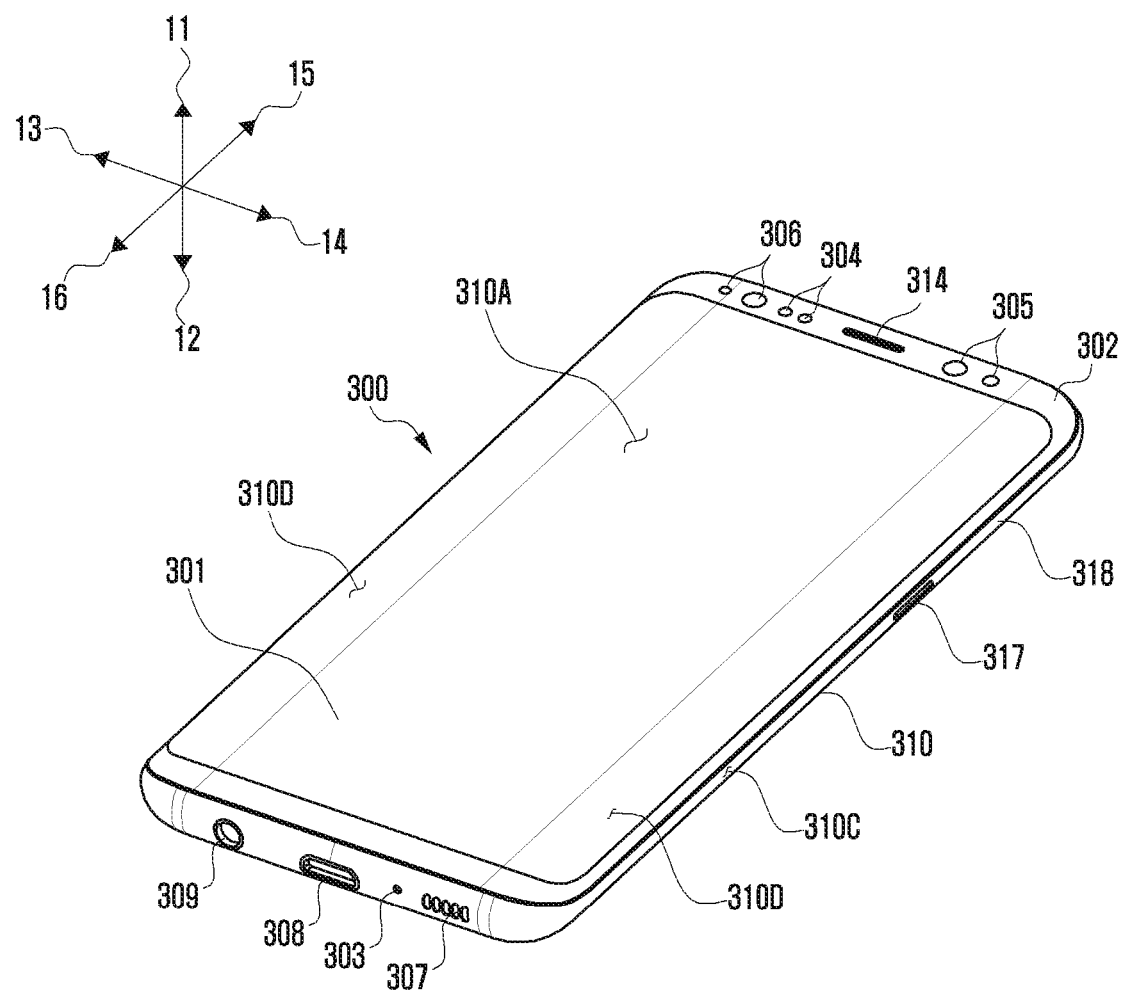
FIG. 3 illustrates an example of a front perspective view of an electronic device according to various embodiments.
Figure 4:
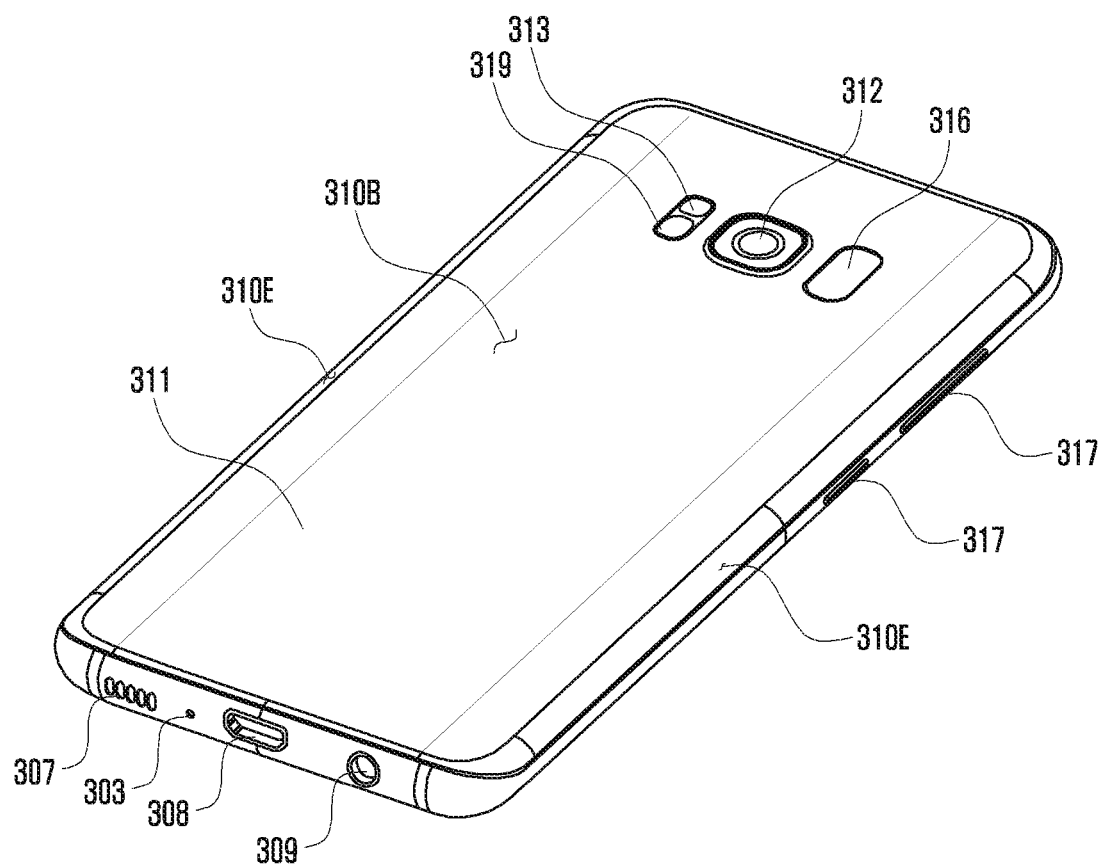
FIG. 4 illustrates an example of a rear perspective view of an electronic device according to various embodiments.

FIG. 3 illustrates an example of a front perspective view of an electronic device according to various embodiments. FIG. 4 illustrates an example of a rear perspective view of an electronic device according to various embodiments.

Referring to FIGS. 3 and 4, an electronic device 300 according to various embodiments may include all or part of the electronic device 101 illustrated in FIG. 1. According to an embodiment, the electronic device 300 may include a housing 310 including a first surface (or a front surface) 310A, a second surface (or a rear surface) 310B, and a side surface 310c surrounding the space between the first surface 310A and the second surface 310B. According to another embodiment (not shown), the housing 310 may have a structure including some of the first surface 310A, the second surface 310B, and the side surface 310C of FIG. 3. According to an embodiment, the first surface 310A may be formed by a front plate 302, at least a portion of which is substantially transparent. The second surface 310B may be formed by a substantially opaque rear plate 311. The side surface 310C may be coupled to the front plate 302 and the rear plate 311 and formed by a side bezel structure (or a "side member") 318. In some embodiments, the rear plate 311 and the side bezel structure 318 may be formed so as to be integrated, and may include the same material (for example, a metallic material such as aluminum).

In the illustrated embodiment, the front plate 302 may include two first areas 310D, which seamlessly extend from the first surface 310A and are bent toward the rear plate 311 at both long edges of the front plate 302. In the illustrated embodiment (for example, FIG. 4), the rear plate 311 may include two second areas 310E seamlessly extending from the second surface 310B and bent toward the front plate 302 at both edges. In some embodiments, the front plate 302 (or the rear plate 311) may include only one of the first areas 310D (or the second areas 310E). According to another embodiment, some of the first areas 310D or the second areas 310E may not be included.

According to an embodiment, the electronic device 300 may include at least one of a display 301 (for example, all or some of the display device 160 of FIG. 1 or 2), audio modules 303, 307, and 314 (for example, the audio module 170 of FIG. 1), sensor modules 304, 316, and 319 (for example, all or part of the sensor module 176 of FIG. 1), camera modules 305, 312, and 313 (for example, all or some of the camera module 180 of FIG. 1), a key input device 317 (for example, all or some of the input device 150 of FIG. 1), a light-emitting device 306, and connector holes 308 and 309. In some embodiments, at least one of the elements (for example, the key input device 317 or the light-emitting device 306) may be omitted from the electronic device 300, or other elements may be further included.

The display 301 may be exposed through, for example, a substantial part of the front plate 302. In some embodiments, at least one of the audio module 314, the sensor module 304, the camera module 305, the fingerprint sensor 316, and the light-emitting device 306 may be included in the rear surface of a screen display area of the display 301. In some embodiments, pulse information may be collected from an action of a user finger touching a sensor (for example, a fingerprint sensor or a biometric sensor) embedded into the display 301, and health information estimated on the basis of the collected pulse information may be displayed through the display 301. In some embodiments, at least a portion of the sensor modules 304 and 319 and/or at least a portion of the key input device 317 may be disposed in the first areas 310D and/or the second areas 310E.

The audio modules 303, 307, and 314 may include a microphone hole 303 and speaker holes 307 and 314. The microphone hole 303 may include a microphone for acquiring an external sound therein. The speaker holes 307 and 314 may include an external speaker hole 307 and a cell receiver hole 314.

The sensor modules 304, 316, and 319 may generate electrical signals or data values corresponding to the internal operational state or the external environmental state of the electronic device 300. The sensor modules 304, 316, and 319 may include, for example, a first sensor module 304 (for example, a proximity sensor) and/or a second sensor module (not shown) (for example, a fingerprint sensor) disposed on the first surface 310A of the housing 310, and/or a third sensor module 319 (for example, a heart rate monitoring (HRM) sensor or a photoplethysmography (PPG) sensor) and/or a fourth sensor module 316 (for example, a fingerprint sensor) disposed in the second area 310B of the housing 310. In some embodiments, the third sensor module 319 (for example, the PPG sensor) may be disposed not only in the second surface 310B of the housing 310 but also in the first area 310A. In some embodiments, for operation of the sensor for measuring (or acquiring) a user's biometric information, at least one of the sensor modules 304, 316, and 319 in the first area 310A and/or the second area 310B or a combination thereof may be used.

The camera modules 305, 312, and 313 may include a first camera device 305 disposed in the first area 310A of the electronic device 300, a second camera device 312 disposed in the second area 310B, and/or a flash 313. The camera modules 305 and 312 may include one or a plurality of lenses, an image sensor, and/or an image signal processor (ISP). The flash 313 may include, for example, a light-emitting diode or a xenon lamp. In some embodiments, two or more lenses (for example, an infrared camera, a wide-angle lens, and a telephoto lens) and image sensors may be disposed on one surface of the electronic device 300. In some embodiments, the camera modules 305, 312, and 313 may be formed to operate as a biometric sensor (for example, an iris sensor) for collecting biometric information of the user or to include the biometric sensor (for example, the iris sensor). In some embodiments, the association between the first camera device 305 and the light-emitting device 306 or between the second camera device 312 and the flash 313 may be used to estimate biometric information of the user (for example, a skin tone and an eye health state).

The key input device 317 may be disposed on the side surface 310C of the housing 310. In some embodiments, the key input device 317 may be implemented in different forms, such as soft keys, on the display 301. In some embodiments, the key input device 317 may include the sensor module 316 disposed on the second surface 310B of the housing 310.

The light-emitting device 306 may be disposed in, for example, the first surface 310A of the housing 310. The light-emitting device 306 may provide, for example, information about the state of the electronic device 300 in the form of light. According to another embodiment, the light-emitting device 306 may provide, for example, a light source linked to the operation of the camera module 305. The light-emitting device 306 may include, for example, an LED, an IR LED, and a xenon lamp.

The connector holes 308 and 309 may include a first connector hole 308 capable of accommodating a connector (for example, a USB connector) for transmitting and receiving power and/or data to and from an external electronic device (for example, the electronic device 102 or 104 of FIG. 1) and a second connector hole 309 (for example, an earphone jack) capable of accommodating a connector for transmitting and receiving an audio signal to and from an external electronic device.

When "measurement", "authentication", or "sensing" is mentioned with the term "unconscious" or without the term, it may mean that biometric information can be acquired from a general usage environment of the electronic device 101 (or a user experience) without direct intent (for example, execution of an application related to biometric measurement or a series of operations related to biometric measurement) of the user to perform biometric measurement.

According to various embodiments, biometric measurement may be divided into conscious authentication based on a user's intent and implicit authentication that requires little or no user intent. According to various embodiments, the biometric measurement based on conscious effort (or conscious authentication) is related to the user's health, and may be performed as a result of direct intentional involvement by of the user. For example, the user can measure blood pressure through a measurement device for a preset time (for example, about 30 seconds) to measure the blood pressure. According to various embodiments, the biometric measurement based on unconsciousness (or implicit authentication) may mean an authentication method capable of overcoming the cumbersome nature of biometric measurement or the tedium thereof due to the measurement time by naturally performing additional biometric measurement in the state in which the user focuses on another main activity (for example, the state in which the user is executing and using an application of the electronic device 101). For example, a representative activity using the electronic device 101 may include a general user experience (UX) such as a call (for example, a voice call or a video call) or photography (for example, a selfie). According to an embodiment, when the user is engaged in an activity, the electronic device 101 may provide meaningful biometric information in addition to a natural and general activity, such as a call or photography, to the user through additional biometric measurement.

Recently, the electronic device 101 has followed a trend in which a user interface (for example, a UI or a GUI) is designed based on serendipity to improve a user experience, and may induce unconscious sensing therethrough. According to various embodiments, when activating (turning on) a camera to use augmented reality (AR), the electronic device 101 may unconsciously sense biometric information on the basis of the sensor during the user's activity, such as automatically tracking a thing (or object). According to various embodiments, when unconsciously sensing biometric information, the electronic device 101 may perform concurrent processing (or merging processing) on various pieces of biometric information (for example, biometric information through the camera or biometric information through the sensor (for example, the PPG sensor).

Figure 5:
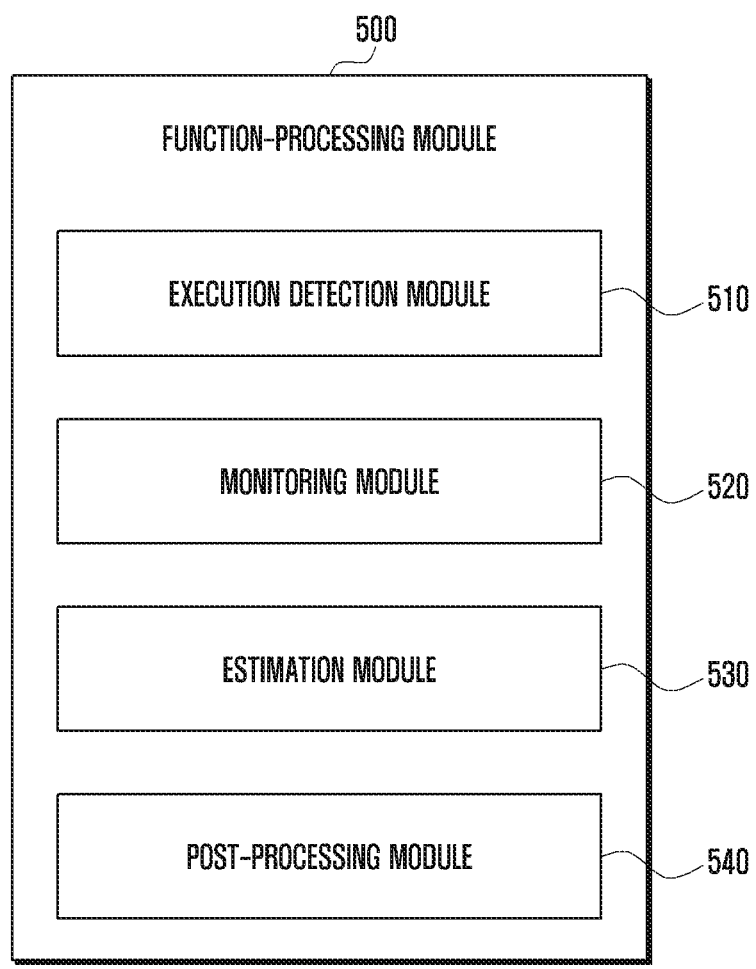
FIG. 5 illustrates an example of a function-processing module in an electronic device according to various embodiments.

FIG. 5 illustrates an example of a function-processing module in an electronic device according to various embodiments.

As illustrated in FIG. 5, FIG. 5 illustrates an example of a function-processing module 500 for executing a function related to acquisition of a user's biometric information in the situation in which the user does not intend to perform biometric measurement (for example, the state in which a function (or an application) related to acquisition of biometric information is not executed) when the user's biometric information is acquired through the electronic device 101 (or the electronic device 300 of FIGS. 3 and 4) according to various embodiments. For example, FIG. 5 illustrates an example of the function-processing module 500 related to estimation of data on user's biometric information through implicit authentication and provision of the data to the user while the user is using the electronic device 101 (for example, a general usage environment (or a general user experience)). According to various embodiments, the function-processing module 500 may be included as a hardware module or a software module in a processor having processing circuitry (for example, the processor 120 of FIG. 1).

Referring to FIG. 5, the function-processing module 500 may include an execution detection module 510, a monitoring module 520, an estimation module 530, and a post-processing module 540.

According to an embodiment, the execution detection module 510 may detect execution of an application in the electronic device 101. The execution detection module 510 may transmit information related to beginning of measurement of the biometric information (for example, a first trigger signal) to the monitoring module 520 in response to detection of execution of the application. According to various embodiments, the execution of the application may include other applications (for example, applications related to photography, phone calls, messaging, the Internet, or settings) which can be executed by the electronic device 101 (or frequently used by the user) other than an application (for example, a health care application) configured to measure the user's biometric information. According to an embodiment, the execution of the application may include the situation in which the user uses (or controls) the electronic device 101 (for example, the user grasps the electronic device 100, the user releases a lock screen, or the user displays a home screen), rather than execution of an application.

According to an embodiment, the monitoring module 520 may monitor whether biometric information is acquired (or input) on the basis of at least one sensor (for example, the sensor module 176 of FIG. 1) in response to execution of the application. According to an embodiment, the monitoring module 520 may monitor at least one sensor and determine whether biometric information is acquired from at least one sensor in response to reception of a first trigger signal from the execution detection module 510. According to an embodiment, the at least one sensor may include a sensor (for example, an image sensor (a camera module or an infrared camera), an iris (or retina) sensor) for acquiring a user's state (for example, a facial image or an eye image), or a sensor (for example, a fingerprint sensor or an electrode) for directly acquiring the user's biometric information. According to various embodiments, the biometric sensor may be disposed at one or more locations at which the user can grasp the biometric sensor on the rear surface of the electronic device 101, within the display device 160 on the front surface, and on the side surface of the electronic device 101. According to various embodiments, the biometric sensor may include a sensor included in an external electronic device (for example, a wearable device), rather than the sensor included within the electronic device 101. For example, biometric information measured through a wearable device worn on the user's body may be received through a communication module and provided to the user.

According to an embodiment, the monitoring module 520 may determine whether biometric information is acquired first through a sensor related to the executed application in response to reception of a trigger signal from the execution detection module 510. For example, when the executed application is a selfie application, biometric information may be monitored through at least one of a sensor (for example, at least one of a camera sensor, a proximity sensor, a fingerprint sensor, an iris recognition sensor, or an electrode) disposed on the front surface of the electronic device 101 (for example, the first surface 310A of FIG. 3) and a sensor (for example, at least one of an HRM sensor, a fingerprint sensor, or an electrode) disposed on the rear surface of the electronic device 101 (for example, the second surface 310B of FIG. 4). According to an embodiment, the monitoring module 520 may transmit information related to beginning of estimation of the biometric information (for example, a second trigger signal) to the estimation module 530 on the basis of the result of monitoring of the biometric information.

According to an embodiment, the estimation module 530 may collect biometric information measured by at least one sensor on the basis of the result of monitoring by the monitoring module 520. According to an embodiment, the estimation module 530 may collect biometric information measured by at least one sensor in response to reception of a second trigger signal from the monitoring module 520. The estimation module 530 may estimate health information on the basis of the collected biometric information. For example, the estimation module 530 may estimate first health information (for example, HR data or $SpO_2$ data) on the basis of at least one piece of the biometric information, and may estimate second health information (for example, stress data) on the basis of at least one piece of the biometric information. For example, the estimation module 530 may estimate each piece of health information on the basis of an estimation condition required for the first health information and the second health information (or a measurement time or an amount of measurement data). According to an embodiment, the estimation module 530 may estimate health information by merging previously accumulated and stored biometric information (or second biometric information or previous biometric information) in addition to the currently measured biometric information (or first biometric information or current biometric information). For example, the estimation module 530 may estimate each piece of health information by merging discontinuous measurement data related to biometric information. According to various embodiments, the merging of the discontinuous measurement data will be described with reference to the drawings below.

According to an embodiment, the post-processing module 540 may perform post-processing to provide (or display) estimated health information to the user. According to an embodiment, the post-processing module 540 may select an area in which the estimated health information is displayed in association with the executed application. When the corresponding health information is provided (or displayed), the post-processing module 540 may perform post-processing such that the displayed health information is augmented (or updated) and provided to the user. According to various embodiments, the operation of post-processing health information will be described below with reference to the drawings.

As described above, the electronic device 101 according to various embodiments of the disclosure may include the sensor module 176, the camera module 180, the display device 160, and the processor 120, wherein the processor 120 is configured to execute an application, acquire first biometric information of a user through the sensor module 176 while an operation related to the application is executed, estimate health information of the user, based on at least the first biometric information, and associate the health information with the operation related to the application and display the health information through the display device 160.

According to various embodiments, the processor 120 may execute a health mode for performing an operation based on first biometric information in the state in which the operation related to the application is maintained in response to detection of the first biometric information from the sensor module 176 while the operation related to the application is being performed.

According to various embodiments, the processor 120 may determine whether there is previously measured second biometric information while the operation related to the application is executed in response to detection of the first biometric information by the sensor module 176.

According to various embodiments, the processor 120 may acquire merged biometric information by merging the previously measured second biometric information and the first biometric information.

According to various embodiments, the first biometric information and the second biometric information may be discontinuous information measured in different contact sessions by the sensor module while the operation related to the application is performed.

According to various embodiments, the processor 120 may reduce an estimation time of the health information on the basis of the merged biometric information.

According to various embodiments, the processor 120 may calculate a measurement time required for the first biometric information, determine at least one piece of health information which can be estimated on the basis of the measurement time, and display a first object related to at least one piece of the health information in a configured area of the display device 160.

According to various embodiments, the processor 120 may augment and display the first object displayed through the display device 160 on the basis of the measurement time, and may additionally display a second object related to the health information through the display device 160 on the basis of the measurement time.

According to various embodiments, a first measurement time for acquiring the first object related to the health information may be shorter than a second measurement time for acquiring the second object related to the health information.

According to various embodiments, the processor 120 may acquire additional third biometric information (for example, voice information and image information) through a module (for example, the camera module 180) or the input device 150 (for example, a microphone)) related to the operation of the application while acquiring the first biometric information through the sensor module 176 so as to concurrently process the first biometric information and the third biometric information.

Figure 6:
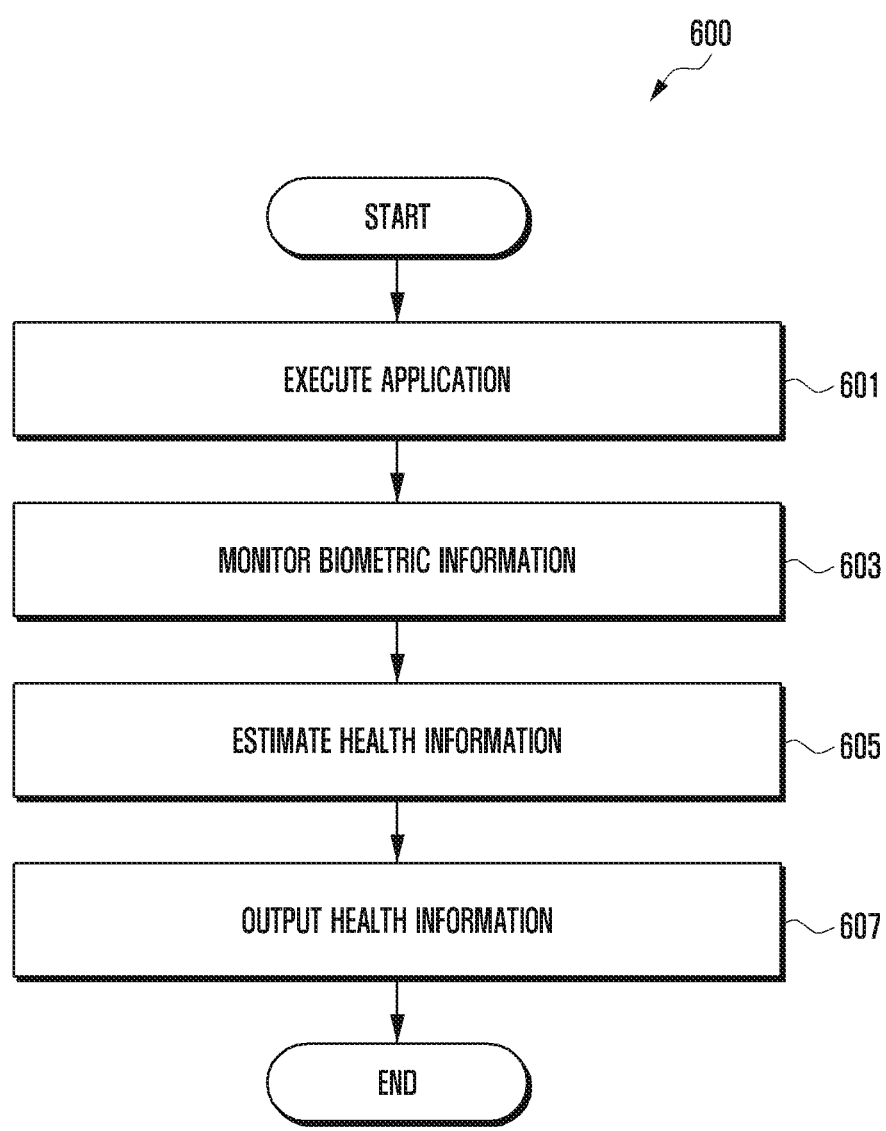
FIG. 6 is a flowchart illustrating a method of operating an electronic device according to various embodiments.

FIG. 6 is a flowchart 600 illustrating a method of operating an electronic device according to various embodiments.

Referring to FIG. 6, in operation 601, the processor 120 of the electronic device 101 (for example, at least one processor including a processing circuit) (or the function-processing module 500 of FIG. 5) may execute an application. According to an embodiment, the user may input an execution command (for example, touch an application icon) for executing the corresponding application to perform a function such as a call or photography (for example, taking a selfie), and the processor 120 may execute the application on the basis of the execution command. The processor 120 may execute the requested application and enter the corresponding mode (for example, a selfie mode or a call mode).

In operation 603, the processor 120 may monitor biometric information. According to an embodiment, the processor 120 may monitor whether biometric information is acquired from at least one sensor in response to execution of the application. For example, the processor 120 may determine whether there is input of biometric information by monitoring a biometric sensor included in the electronic device 101. According to an embodiment, the user may bring a finger, which is a body part, close to or into contact with the biometric sensor, and the biometric sensor may generate an event according to the proximity or contact of the object (for example, the finger) and transmit the event to the processor 120. The processor 120 may monitor biometric information on the basis of the event of the biometric sensor.

In operation 605, the processor 120 may estimate health information. According to an embodiment, the processor 120 may collect biometric information measured by at least one sensor and estimate health information on the basis of at least some pieces of the collected biometric information. According to an embodiment, the processor 120 may estimate first health information on the basis of at least some pieces of the biometric information and estimate second health information on the basis of at least some pieces of the biometric information. The first health information and the second health information may have different required measurement conditions (or measurement times or amounts of measurement data). According to various embodiments, when there is second biometric information (for example, biometric information previously measured and stored in a memory (for example, the memory 130 of FIG. 1) related to the currently measured first biometric information, the processor 120 may estimate health information by merging the second biometric information and the first biometric information. For example, the processor 120 may estimate each piece of health information by merging discontinuous measurement data (for example, the first biometric information and the second biometric information) related to the biometric information. According to various embodiments, it may be possible to measure various kinds of health information through the sensor, as shown in [Table 1] below, and respective pieces of health information (for example, measurement items) may be measured for different durations of time as required, and some pieces of health information may require the same or similar durations of time.

TABLE 1

| Measurement item | Contents | Time required for initial measurement |
|---|---|---|
| Heart Rate | Heart rate per minute Measurable by PPG, ECG, and camera | 5 to 20 seconds |
| SpO$_2$ | Oxygen saturation in blood - measurable by PPG sensor (plurality of wavelengths) | 5 to 20 seconds |
| Heart Rate Variation | Heart-rate variability - measurable by PPG, ECG, and camera | 5 to 20 seconds |
| Blood pressure | Systolic blood pressure (SBP), diastolic blood pressure (DBP), mean arterial pressure (MAP) - estimate blood pressure through analysis of waveform of PPG signal or measurement of pulse transition time through plurality of sensors | 30 seconds to 1 minute |

TABLE 1-continued

| Measurement item | Contents | Time required for initial measurement |
|---|---|---|
| Stress | Measurement on PPG, heart rate of ECG, and heart-rate variability -accuracy improved when information such as blood pressure is added | 20 seconds to 1 minute |
| Blood Glucose | Measure glucose concentration in blood - measurable by PPG sensor | 30 seconds to 1 minute |
| Body Composition | Quantitatively provide body components - measurable by electrode (bioelectrical impedance method) | 5 to 20 seconds |
| Skin | Detect skin tone, wrinkles, red spots, and acne through camera | Less than 5 seconds |
| Emotion | Measure emotional state by analyzing information measured by sensor (PPG or ECG) and feature points of face acquired by camera | Longer than or equal to 1 minute |

In operation 607, the processor 120 may output health information. According to an embodiment, the processor 120 may perform post-processing to provide (or display) at least one piece of the estimated health information to the user. For example, the processor 120 may select an area in which the estimated health information is displayed in association with the executed application, convert the health information into a relevant object (or item) (for example, text, a number, an icon, a graph, or a waveform), and provide (or display) the object in the selected area.

Figure 7A:
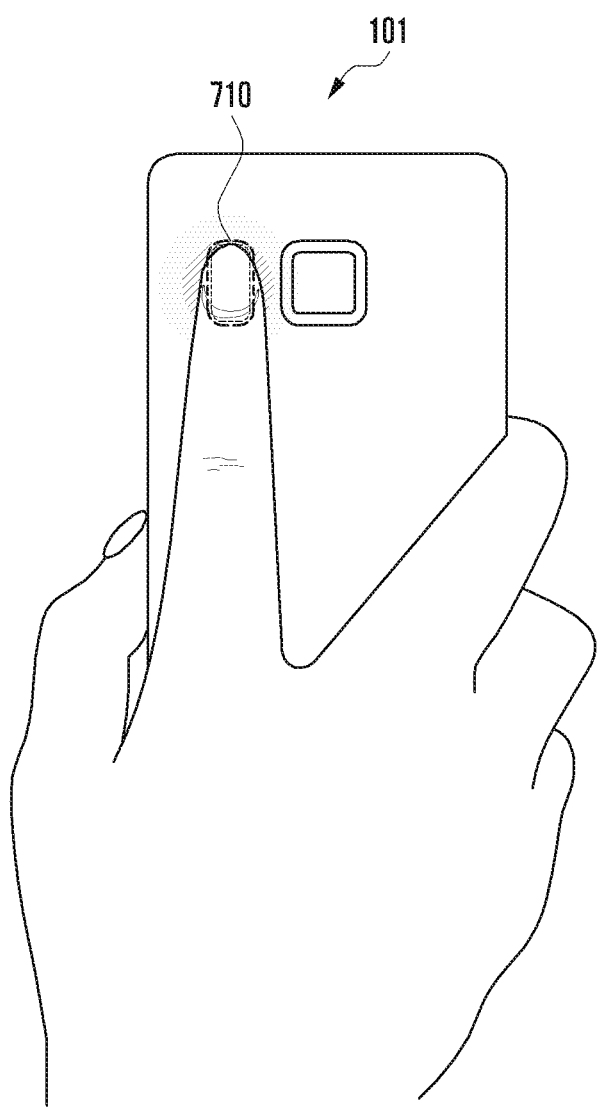
FIGS. 7A and 7B illustrate an example in which an electronic device measures biometric information according to various embodiments.
Figure 7B:
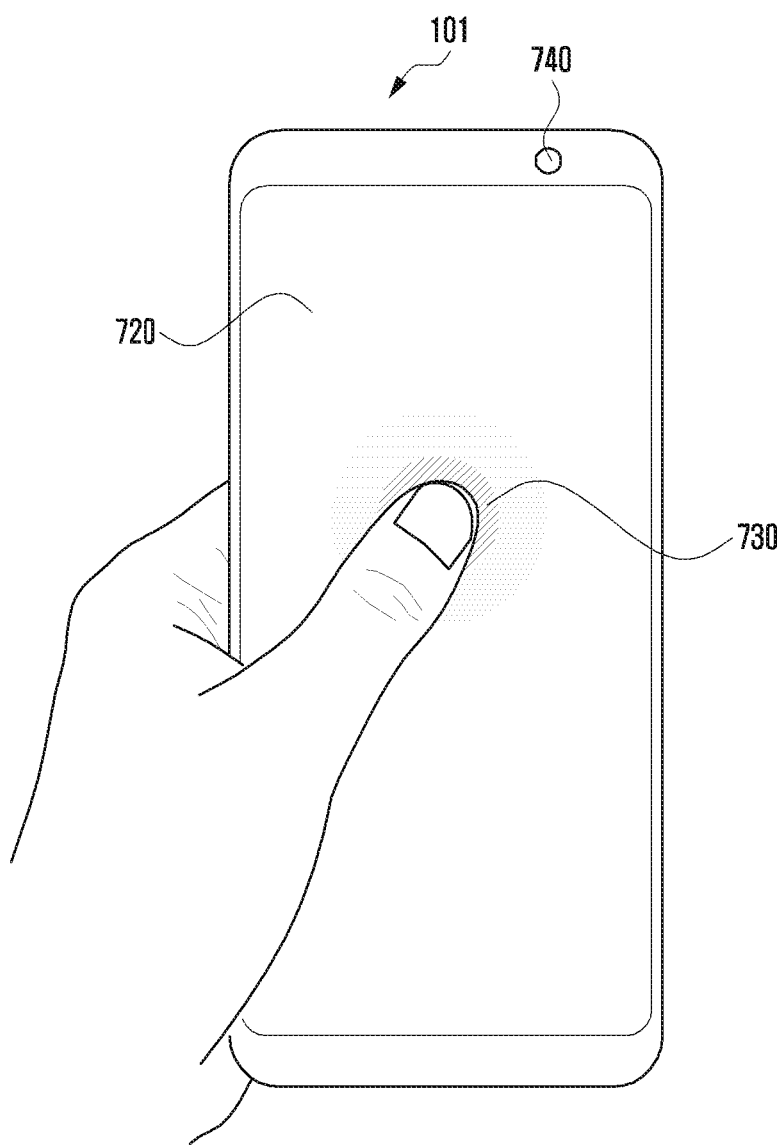

FIGS. 7A and 7B illustrate examples in which an electronic device measures biometric information according to various embodiments.

As illustrated in FIGS. 7A and 7B, measurement of biometric information by the electronic device 101 according to various embodiments may vary depending on the location of the sensor. According to an embodiment, an ergonomic position may be determined so as not to influence the execution mode of the application (for example, a selfie mode or a call mode).

For example, as illustrated in FIG. 7A, a method of measuring biometric information through a rear sensor 710 (for example, a PPG sensor) of the electronic device 101 may be included. According to an embodiment, when an index finger approaches the rear sensor 710 (for example, the PPG sensor) disposed on the rear surface of the electronic device 101, it may be determined whether an object (for example, the index finger) is in proximity to or contacts the rear sensor 710, and a biometric information measurement operation may be performed through the rear sensor 710 on the basis of the result. For example, various pieces of biometric information as shown in [Table 1] may be measured in a one-time touch state. According to an embodiment, the measurement time may vary for each measurement item (for example, health information).

For example, as illustrated in FIG. 7B, a method of measuring biometric information through a biometric sensor (not shown) on a display 720 (for example, the display device 160 of FIG. 1) of the electronic device 101 may be included. For example, electrocardiography (ECG) measurement can be performed through a transparent electrode 730 additionally configured on a layer of the display 720. In another example, photoplethysmography (PPG) measurement can be performed through an RGB LED of the display 720 and the rear sensor 710 on the rear surface.

According to various embodiments, the biometric sensor may include, for example, a PPG sensor and an ECG sensor. According to an embodiment, the PPG sensor may radiate infrared (IR) light or visible light (red, green, or blue) to a body part and measure a reflected signal through a photodiode so as to measure a biometric state (for example, a heart rate) on the basis of the shape of a signal pattern or a change over time. According to an embodiment, the ECG sensor using an electrode uses a different scheme from the PPG sensor, but may obtain the same measurement of the user's heart rate as the ECG sensor. The electrode may be located on at least a portion of the front surface, the rear surface, or the side surface of the electronic device 101, and may be configured as a transparent electrode 730 on the display 720 and enable biometric measurement through a screen.

According to various embodiments, biometric information may be measured using a camera (for example, an image sensor). For example, when a front camera 740 is activated, a pattern of blood vessels in a face, which is not visible to the user's eyes, may be captured by the camera, and the heart rate may be measured on the basis thereof.

According to various embodiments, respective sensors (for example, biometric sensors 710 and 730 and a front camera 740) may have different accuracies depending on the measurement environment and sensor capability. Accordingly, even though various sensors can be selected, the sensor having the best capability may be selected, or a measurement value may be determined more accurately and rapidly through a combination of a value measured by one sensor and another value. According to various embodiments, it may be possible to measure various kinds of health information through at least one sensor, as shown in [Table 1].

According to various embodiments, the user may execute an application related to a specific function such as "call" or "camera" and use the corresponding function. According to various embodiments, while the user is having a general user experience as described above, biometric information suitable for the corresponding user experience (for example, the executed application) may be measured.

According to an embodiment, when the user poses for a selfie and activates a selfie camera (for example, the front camera), the electronic device 101 may enter a selfie mode. When the user brings a finger into contact with a sensor attached to the rear surface of the electronic device 101, the electronic device 101 may enter a health mode, in addition to the selfie mode (or in the state in which the selfie mode is maintained). For example, the selfie mode may be provided as a foreground process, and the health mode may be provided as a background process. According to an embodiment, when the user's finger is not recognized through the biometric sensor, the electronic device 101 may maintain the selfie mode.

According to various embodiments, in addition to the selfie mode, biometric information may also be measured when a phone call (in, for example, a voice call mode or a video call mode) is made. Taking a selfie or making a phone call may be the functions that are most frequently used by the user and a user-oriented function based on a user experience. Further, image information of the user captured through the camera and user information that can be sensed during a phone call (for example, image information in a video call) may be frequently acquired. Accordingly, this may be the most natural scenario to measure and associate biometric information related to the user, and may entail little reluctance or impose only slight inconvenience in measurement of the user's biometric information.

FIG. 8 illustrates an example in which an electronic device estimates health information according to various embodiments.

As illustrated in FIG. 8, FIG. 8 illustrates an example of measuring a user's biometric information on the basis of a biometric sensor (for example, a PPG sensor) located on the rear surface of the electronic device 101 in a selfie mode, measuring relevant health information, and providing the health information to the user. According to various embodiments, when a condition of execution of an application (for example, the selfie mode) satisfies conditions for measuring the user's biometric information, measurable biometric information is collected (aggregated) and health information may be augmented on the basis of the biometric information.

Referring to FIG. 8, an element A of FIG. 8 may indicate an example of the state in which the user executes a selfie mode. According to an embodiment, the electronic device 101 may activate a front camera 810 of the electronic device 101 in response to execution of the selfie mode, acquire (or capture) a user's image 820 (for example, a selfie image) through the front camera 810, and display the user's image as a preview on the display device 160 (for example, the display 210).

An element B of FIG. 8 may indicate an example of the state in which the user brings a finger into contact with a biometric sensor 830 on the rear surface of the electronic device 101 while the selfie mode is executed. According to an embodiment, the electronic device 101 may detect an event (for example, detection of biometric information) due to contact by the finger from the biometric sensor 830 while the selfie mode is executed. According to an embodiment, the electronic device 101 may acquire biometric information through the biometric sensor 830 in response to detection of the event.

Referring to element C, element D, and element E of FIG. 8, when biometric information is detected by the biometric sensor 830 while the selfie mode is executed, the electronic device 101 may operate a camera 810 for the selfie mode and concurrently measure biometric information through the biometric sensor 830. According to an embodiment, the electronic device 101 may measure various pieces of biometric information as shown in [Table 1] above and estimate health information on the basis of the biometric information. According to an embodiment, the electronic device 101 may sequentially provide the user with the corresponding health information on the basis of the measurement time required for each piece of the health information. According to an embodiment, the electronic device 101 may sequentially estimate at least one piece of health information requiring a short measurement time and visually provide the user with the health information through the display device 160.

According to an embodiment, as exemplified by element C of FIG. 8, the electronic device 101 may estimate first health information (for example, heart-rate information (for example, a required measurement time of about 5 to 20 seconds) that first (or initially) satisfies a condition (for example, a required measurement time or a required number of measurements) (or that has a short measurement time) at an early stage. The electronic device 101 may display a first object 840 (for example, an icon including numerical data) related to estimated heart-rate information in an area on the display device 160 (for example, an area configured to display heart-rate information). According to an embodiment, the electronic device 101 may overlay the first object 840 on the selfie image 820 and provide the same.

According to an embodiment, as exemplified by the element D of FIG. 8, when a first state, in which an object (for example, a finger) contacts the biometric sensor 830 (for example, attached session), is maintained (for example, when a required measurement time during which second health information can be measured is satisfied), the electronic device 101 may estimate the second health information (for example, blood pressure) of which the required measurement time is subsequently satisfied (for example, required measurement time: about 30 seconds to 1 minute). The electronic device 101 may display a second object 850 related to the estimated blood pressure information in an area (for example, an area configured to display the blood pressure information) of the display device 160. According to an embodiment, the electronic device 101 may overlay the second object 840 on the selfie image 820 and provide the same. For example, the electronic device 101 may create an effect of turning the user's face red according to the blood pressure information.

According to an embodiment, as exemplified by the element E of FIG. 8, when a first state, in which an object (for example, a finger) contacts the biometric sensor 830 is maintained (for example, when a required measurement time during which third health information can be measured is satisfied), the electronic device 101 may estimate the third health information (for example, emotion information (for example, a required measurement time of about 1 minute or more) for which the required measurement time is subsequently satisfied. According to an embodiment, the emotion information may indicate a user's emotional state (for example, calm, angry, sad, or gloomy). The electronic device 101 may display a third object 860 related to the estimated emotion information (for example, an icon (or emoticon) corresponding the emotional state) in an area (for example, an area configured to display the emotion information) of the display device 160.

According to an embodiment, as exemplified by the element F of FIG. 8, the user may remove the finger contacting the biometric sensor 830 while the selfie mode is maintained. According to an embodiment, the electronic device 101 may detect release of the first state (for example, detached session) and switch to a second state (for example, a state in which the finger does not contact the biometric sensor 830).

According to an embodiment, as exemplified by the element G of FIG. 8, when the first state (for example, the state of being touched by the user) is released, the electronic device 101 may store relevant information (for example, state information and time information). For example, the electronic device 101 may store the measured biometric information (for example, biometric data included in the biometric information (for example, raw data), associate (or map) types of the health information provided to the user (for example, first health information, second health information, and third health information) with the time at which the corresponding health information was measured, and store the same. According to an embodiment, the biometric data (for example, raw data) may include time information corresponding to a measurement time (or a signal length, (for example, a wavelength).

According to an embodiment, when the electronic device 101 completes storage of the relevant information (for example, state information and time information), the electronic device 101 may provide a fourth object 870 (for example, a call icon or a call menu) for calling the stored information. According to an embodiment, the fourth object 870 may be provided as a command for storing the information in order to store the relevant information according to a user's selection. For example, when the first state is released, the electronic device 101 may provide the fourth object 870 before storing the relevant information, and then the user may selectively store the relevant information. According to various embodiments, even when the relevant information is selectively stored by the user, the biometric data may be continuously (or automatically) stored in the background.

According to various embodiments, the electronic device 101 may execute the application as illustrated in FIG. 8, associate (or map) the application with relevant information, and then store the same while the application is executed. According to an embodiment, when content such as a photo or a video is generated through the selfie mode, the electronic device 101 may associate (or map) meta information of the generated content with relevant information and store the same. According to another embodiment, when a call (for example, a voice call or a video call) is performed through the call mode, the electronic device 101 may associate (or map) a call log with relevant information and store the same.

According to various embodiments, the biometric sensor may include various sensors capable of measuring at least one of a biometric physical change or a chemical change, and may include, for example, an optical sensor, an electrical signal measurement sensor, and a pressure sensor.

According to various embodiments, a health-sensing model obtained on the basis of a signal measured by the biometric sensor may be included. For example, signals of various wavelengths may be extracted by one PPG sensor, and various pieces of biometric information may be extracted on the basis of a characteristic of reflecting LEDs of each wavelength. Hereinafter, the optical sensor will be described as an example of the health-sensing model that can be obtained.

Figure 9:
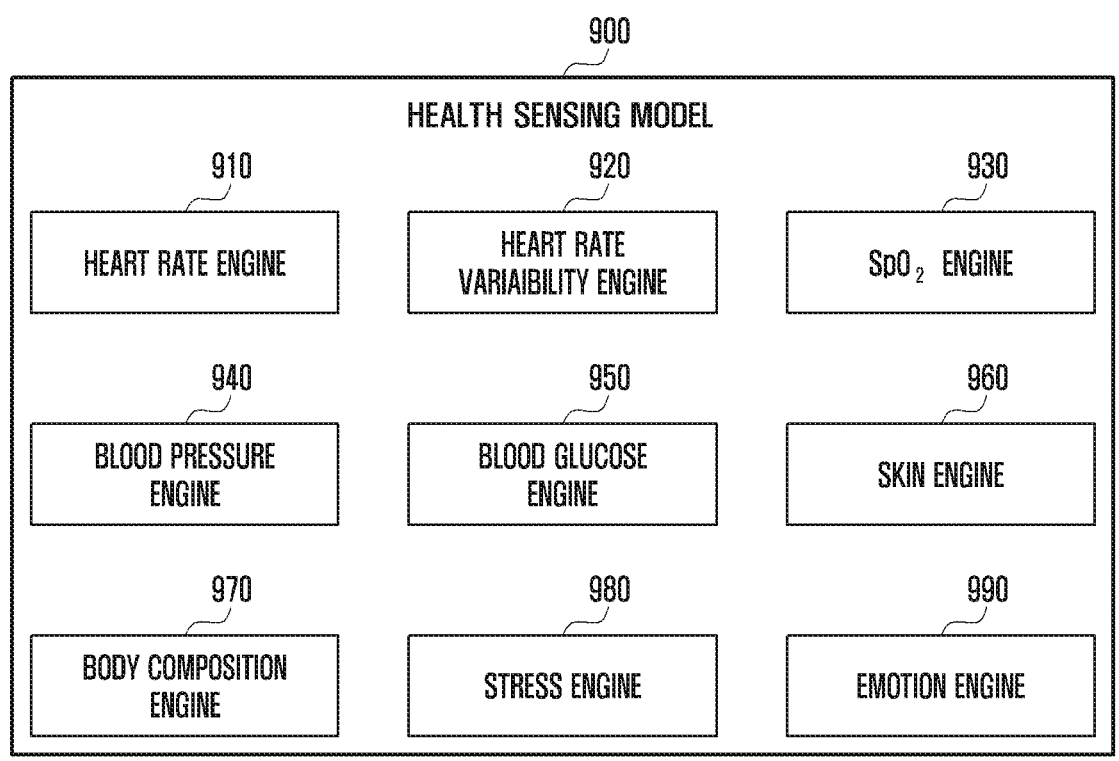
FIG. 9 illustrates an example of a health-sensing model in an electronic device according to various embodiments.

FIG. 9 illustrates an example of a health-sensing model in an electronic device according to various embodiments.

Referring to FIG. 9, according to an embodiment, when a selfie is taken, a sensor (for example, the biometric sensor) may use the selfie operation as a trigger and accordingly induce the user to naturally put his/her finger on the biometric sensor.

According to various embodiments, the electronic device 101 may measure or collect a user's image (for example, a selfie image) and biometric information from a camera (for example, a front camera) and a sensor (for example, the biometric sensor) while the user's finger is located on the sensor.

According to various embodiments, the biometric information that can be measured by the sensor may include, for example, a heart rate (HR), heart rate variation (HRV), oxygen saturation ($SpO_2$), blood pressure (BP), blood glucose (BG), stress, emotions, or skin hydration, as shown in [Table 1]. According to various embodiments, the electronic device 101 (or the sensor of the electronic device 101) may include a health-sensing model related to measurement of the biometric information.

As illustrated in FIG. 9, a health-sensing model 900 of the sensor (for example, the optical sensor) may include, for example, a heart rate engine 910, a heart-rate variability engine 920, an $SpO_2$ engine 930, a blood pressure engine 940, a blood glucose engine 950, a skin engine 960, a body composition engine 970, a stress engine 980, or an emotion engine 990.

According to various embodiments, an example of measuring biometric information on the basis of the health-sensing model 900 of the optical sensor will be described.

According to an embodiment, the heart rate (HR) and the heart-rate variability (HRV) may be determined based on a signal, obtained by the optical sensor, by the heart rate engine 910 and the heart-rate variability engine 920. According to an embodiment, the $SpO_2$ may be measured by the $SpO_2$ engine 930 through the optical sensor, which is capable of performing measurement in two or more wavelengths.

According to an embodiment, the blood pressure (BP) may be estimated by the blood pressure engine 940 through pulse wave analysis (PWA) of the signal measured by the optical sensor. For example, the BP may be estimated by extracting various feature points from the measured waveforms and substituting corresponding feature points for a predetermined model (for example, the blood pressure engine 940). Further, the BP may be estimated by measuring minute changes in face color from the image acquired by the camera (for example, a front camera or a selfie camera), extracting a waveform in real time, and measuring a transit time (for example, a pulse transit time (PTT)) difference from the signal measured by the optical sensor. In addition, the BP may be estimated using the two methods together.

According to an embodiment, for the blood glucose (BG), a change in glucose concentration within the blood may be estimated by extracting an absorption level and feature points of the signal measured by the optical sensor, which is capable of performing measurement in two or more wavelengths.

According to an embodiment, for the skin, the skin engine 960 may quantify skin tone, wrinkles, red spots, or acne in real time by analyzing a user's facial image (for example, a selfie image) acquired from a camera (for example, a front camera).

According to an embodiment, the body composition (for example, body water, body fat, and muscle mass) may be estimated by analyzing biometric electric resistance measured from an electrode through the body composition engine 970. For example, when the current passes through various body parts, a voltage drop may occur. At this time, indirect information on a physical characteristic of the corresponding part may be acquired through the measured magnitude of the voltage drop, and body water and fat may be quantified based thereon.

According to an embodiment, the stress may be estimated by analyzing a change aspect for a predetermined time on the basis of the pre-measured HR/HRV through the stress engine 980. According to an embodiment, the accuracy of estimation of stress may be improved by reflecting BP information in the change aspect for a predetermined time.

According to an embodiment, the emotion may be digitized by estimating an emotion such as happiness, sadness, or anger of the user by extracting features of a user's facial expression from the image (for example, a selfie image) acquired from the camera, in addition to the biometric information measured through the emotion engine 990. According to an embodiment, the emotion engine 990 may detect a specific emotion of the user (for example, tension or excitement) on the basis of measurement information of the stress and/or heart rate.

According to various embodiments, the electronic device 101 may perform a post-processing operation on a camera image as well as measured biometric information while the user's finger contacts the sensor (for example, the biometric sensor). According to an embodiment, the electronic device 101 may display only biometric information which is reliable and measurable to the user on the basis of the time (or the contact time) during which the user's finger is located on the sensor during the post-processing operation.

According to an embodiment, the electronic device 101 may first perform post-processing on biometric information that can be measured for a first time (for example, a short time) and sequentially augment available biometric information. For example, the heart rate (HR) or the oxygen saturation ($SpO_2$) may be estimated for a short time (for example, about 5 to 20 seconds). For example, when biometric information is further measured for a second time (for example, a time longer than the first time) after the first time, information such as heart-rate variability (HRV), stress, blood pressure (BP), or blood glucose (BG) may be sequentially (or a plurality of pieces of health information may be substantially concurrently) estimated in chronological order. For example, when biometric information is further measured for a third time (for example, a time longer than the second time) after the second time, information such as emotion information may be estimated.

Hereinafter, an example of estimating health information according to a trigger (or an event) related to estimation of each piece of health information on the basis of the health-sensing model described in the various embodiments above will be described.

Figure 10:
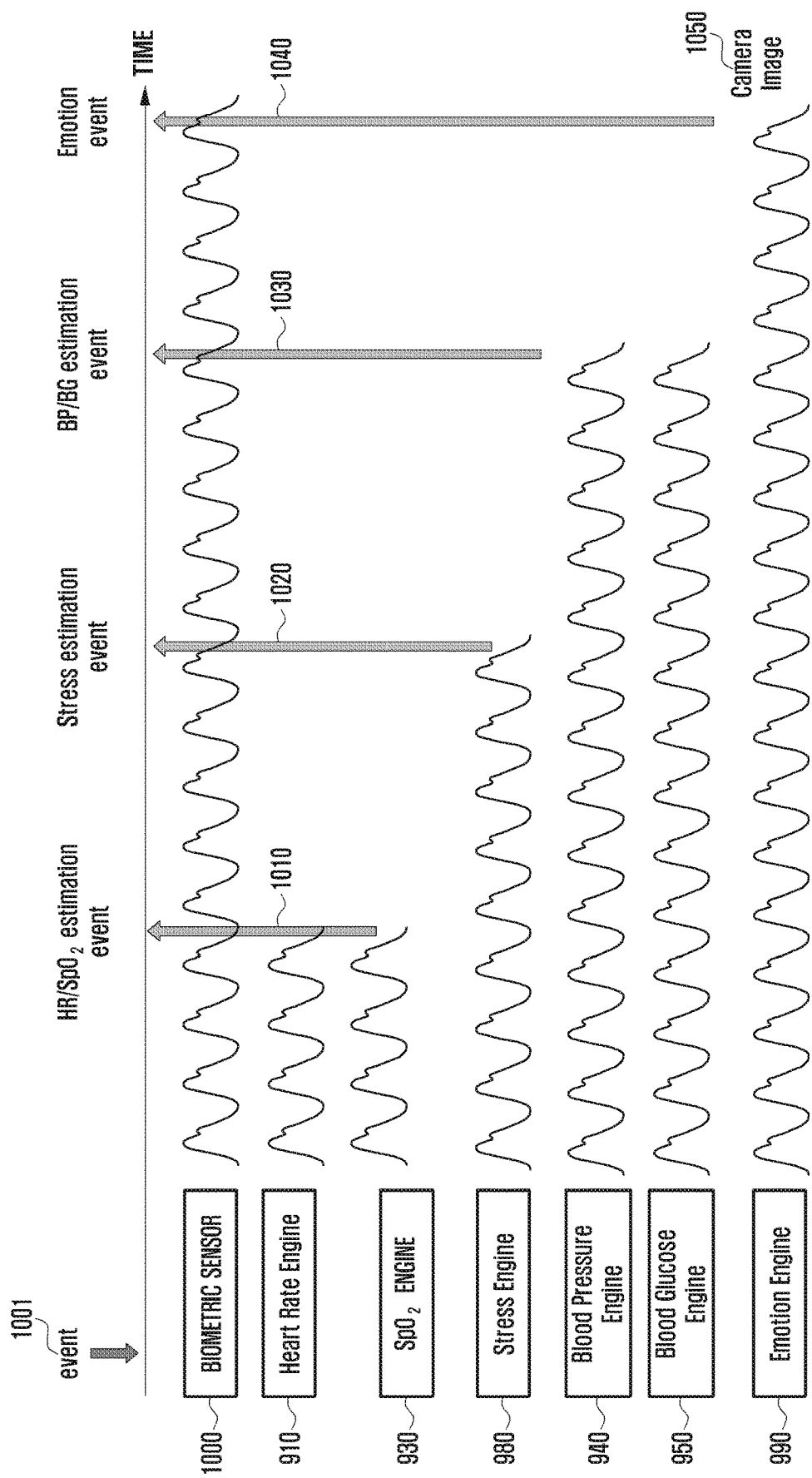
FIG. 10 illustrates an example in which an electronic device estimates health information according to various embodiments.

FIG. 10 illustrates an example in which an electronic device estimates health information according to various embodiments.

Referring to FIG. 10, FIG. 10 illustrates an example in which a measurement event for each piece of health information is generated on the basis of the health-sensing model illustrated in FIG. 9.

According to an embodiment, the electronic device 101 may extract M pieces of health information (or biometric data) (for example, a heart rate (HR), stress, blood glucose (BG), blood pressure (BP), and emotion) from N biometric sensors (for example, a PPG sensor, an electrode, an image sensor (for example, a camera), or an acceleration sensor (accelerometer)). According to an embodiment, the number of pieces of health information that can be measured on the basis of one biometric sensor may be plural, and, for example, the number M of pieces of health information may be equal to or larger than the number N of biometric sensors (for example, N≤M).

According to various embodiments, the electronic device 101 may simultaneously extract various models, and thus various engines (for example, the heart rate engine, the stress engine, the blood glucose engine, the blood pressure engine, and the emotion engine) may operate simultaneously. According to various embodiments, input signals of the respective engines may be the same, but a result event may be transmitted at a different time point since a processing engine is independently driven. For example, the number of input signals (for example, events 1001) made through a biometric sensor 1000 (for example, a PPG sensor) may be one, and engines which may be capable of operating on the basis of the input signal from the biometric sensor 1000 may be plural (for example, the heart rate engine 910, the oxygen saturation ($SpO_2$) engine 930, the stress engine 980, the blood pressure engine 940, the blood glucose engine 950, and the emotion engine 990). According to various embodiments, a plurality of engines may operate independently, and may generate measurement events at respective time points on the basis of at least the reference time (or minimum time) required to estimate the corresponding health information.

As illustrated in FIG. 10, according to an embodiment, the electronic device 101 may first generate an event related to heart rate (HR) information on the basis of the heart rate engine 910 at a first time 1010. According to various embodiments, the heart-rate information should be continuously monitored in real time, and thus the heart rate engine 910 may continuously transmit a relevant event to the processor 120 after an initial event. According to an embodiment, the heart-rate variability and the oxygen saturation may have substantially the same (or similar) measurement time. According to an embodiment, an event related to oxygen saturation information and an event related to heart-rate variability information may be substantially simultaneously generated at the first time 1010 by the oxygen saturation engine 930 and the heart-rate variability engine 920 (not shown in FIG. 10). According to an embodiment, the heart-rate variability measurement becomes more accurate as the observation time is longer, and thus an event transition time thereof may be later than the heart rate. For example, the heart-rate variability may be more accurate as the number of pieces of biometric information collected for calculation is larger, and thus an appropriate determination time may be later than the heart rate in the interest of reliability.

According to an embodiment, the electronic device 101 may generate an event related to stress information on the basis of the stress engine 980 at the second time 1020. According to various embodiments, the stress engine 980 may measure stress on the basis of the heart-rate variability. According to an embodiment, the electronic device 101 may measure stress on the basis of incomplete heart-rate variability (for example, heart-rate variability at the first time 1010) in order to display stress information on the screen displayed through the display device 160 (for example, an application execution screen, for example, a screen corresponding to the selfie mode or a screen corresponding to the video call mode) and display the stress through a variable object (for example, a GUI object, a stress level of which is variable) of which the accuracy increases on the basis of a contact (attached) time (for example, a time later than the first time 1010) between the finger and the biometric sensor 1000. For example, when information (or an object) related to health information is displayed on the screen, an accurate number (for example, a quantitative value) of the corresponding health information is not displayed, but a trend (for example, a qualitative value) of the health information may be displayed to guide (coach) the corresponding health information to the user. For example, in the case of providing guidance of health information, the user has low sensitivity to accuracy or reliability of health information, and thus it may be possible to display the corresponding health information even for a short measurement time.

According to an embodiment, the electronic device 101 may generate an event related to blood pressure information on the basis of the blood pressure engine 940 at third time 1030. According to an embodiment, the electronic device 101 may also generate an event related to blood glucose information on the basis of the blood glucose engine 950 at the third time 1030. According to an embodiment, it is important for blood pressure to extract an optimal signal waveform, and thus representativeness or statistical reliability of waveforms should be increased through acquisition of a plurality of waveforms. According thereto, the measurement time (for example, the time at which the event is generated) may be very short, or may be long.

According to an embodiment, the electronic device 101 may generate an event related to emotion information on the basis of the emotion engine 990 at a fourth time 1040. According to an embodiment, since the emotion may be associated with stress, the event may be provided in response to the stress value. According to an embodiment, the electronic device 101 may express complex and detailed emotions rather than fragments of emotional state by combining a user's voice and facial expression information. For example, in the selfie mode, image information (for example, a camera image 1050) may be acquired through an image sensor (for example, a camera), a user's emotional state may be determined on the basis of the acquired image information and biometric information (for example, stress information) by the biometric sensor 1000, and the user's emotional state may be determined on the basis of voice information and biometric information during a call.

According to various embodiments, various measurement engines related to measurement of the user's biometric information illustrated in FIGS. 9 and 10 may have different measurement schemes and conditions required for measurement (for example, required measurement times) according to respective measurement engines. Accordingly, the measurement events related to the respective measurement engines in FIG. 10 may be sequentially generated in the order in which conditions of the measurement engines are satisfied (met), and the time point at which the measurement event is generated may vary depending on the situation.

According to an embodiment, the accuracy of the heart rate or the heart-rate variability may increase as the number of pieces of sampling data used for measurement increases, and thus a method requiring a predetermined time may be included. According to an embodiment, the oxygen saturation (SpO$_2$) may include a method of detecting all of biometric changes under two kinds of light, namely infrared (IR) light and red light. For example, the heart rate, the heart-rate variability, or the oxygen saturation may have a basic time for sequential measurement. According to an embodiment, the blood pressure or the blood glucose may have a method requiring one complete (or clean (for example, having no noise)) waveform, but the complete waveform may not be acquired at one time depending on the measurement situation. As described above, each measurement engine has a minimum time and a maximum time required for measurement, which vary depending on the situation. Accordingly, the measurement event related to each measurement engine may differ in various situations, such as the measurement environment or whether to match with a pre-measured signal waveform.

FIG. 10 illustrates an example of executing an application, measuring biometric information at a corresponding time point, and generating respective measurement events related to health information at the configured corresponding time. According to various embodiments, it is possible to accumulate (or store) and manage biometric information (for example, biometric data, raw data, or source data) acquired (or measured) during execution of an application, and to reduce the amount of time during which the measurement event of relevant health information is generated on the basis of the accumulated data when the measurement event is generated. For example, the electronic device 101 may generate an event related to health information by merging discontinuous measurement data. Hereinafter, an example in which the electronic device 101 merges discontinuous measurement data will be described with reference to FIGS. 11 to 13.

Figure 11:
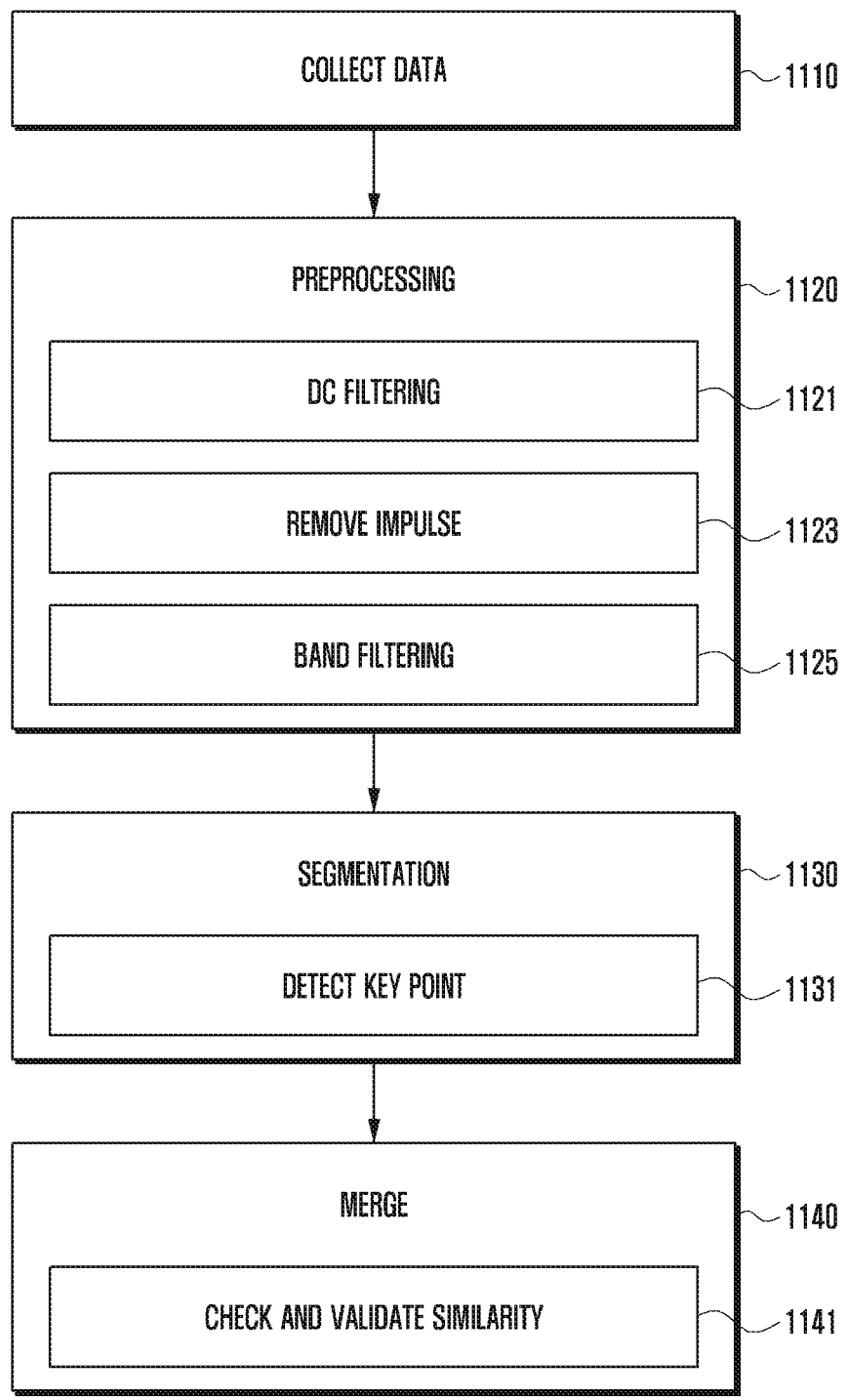
FIG. 11 illustrates an example in which an electronic device merges discontinuous measurement data according to various embodiments.

FIGS. 11 and 12 illustrate an example in which an electronic device merges discontinuous measurement data according to various embodiments.

As illustrated in FIGS. 11 and 12, FIG. 11 illustrates an operation of merging discontinuous measurement data, and FIG. 12 illustrates an example of the text result through discontinuous measurement of real data (for example, a PPG signal).

Referring to FIGS. 11 and 12, in operation 1110, the processor 120 of the electronic device 101 (or the function-processing module 500 of FIG. 5) may collect data related to health information (for example, raw data). According to various embodiments, the raw data is data which can be received by the electronic device 101 through a biometric sensor of the electronic device 101, and may include, for example, biometric information that has not been processed, before being processed as health information. According to an embodiment, as illustrated in FIG. 12A, an input signal transmitted from a biometric sensor according to contact between a user's finger and the biometric sensor (for example, a PPG sensor) may be included. According to an embodiment, FIG. 12A illustrates an example in which discontinuous raw data (for example, a raw PPG signal) is input as the user repeatedly brings a finger into contact with the biometric sensor (an attached state) and removes the finger therefrom (a detached state). For example, FIG. 12A illustrates an example of a discontinuous input signal (for example, a discontinuous PPG signal).

In operation 1120, the processor 120 may perform pre-processing on the basis of the collected data. According to an embodiment, the pre-processing operation 1120 may include a direct-current (DC) filtering operation 1121, an impulse removal operation 1123, and a band-pass filtering operation 1125.

Figure 12A:
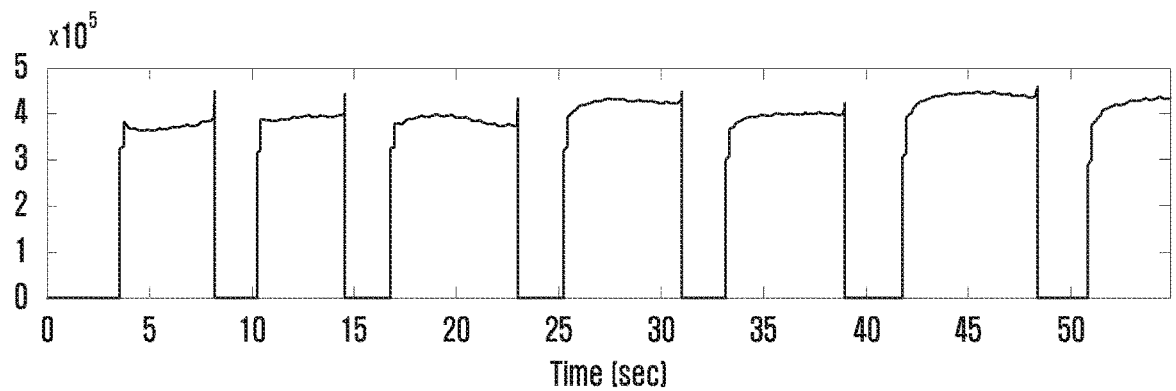
FIGS. 12A, 12B, 12C, and 12D illustrate an example in which an electronic device merges discontinuous measurement data according to various embodiments.
Figure 12B:
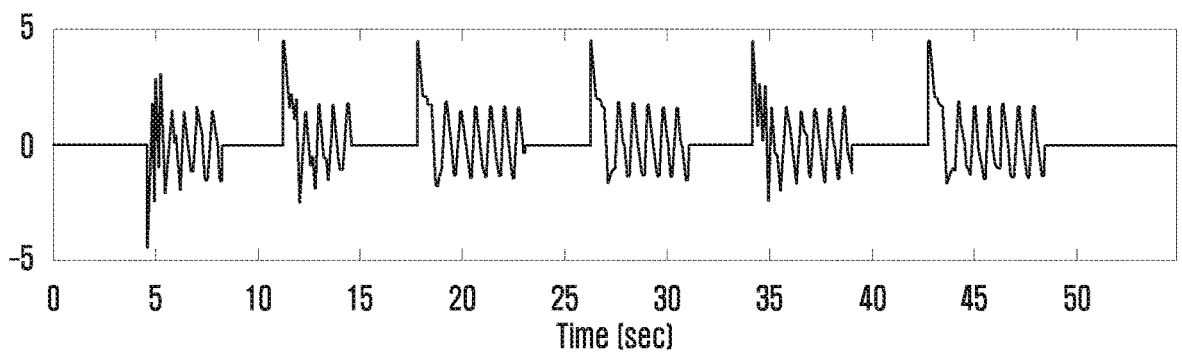

According to an embodiment, in operation 1121, the processor 120 may block a DC component by filtering the DC component from the input signal, and may output only an alternation current (AC) component from the input signal. According to an embodiment, in operation 1120, the processor 120 may remove impulse noise from the AC component. For example, the processor 120 may remove a false edge generated by impulse noise. According to an embodiment, in operation 1125, the processor 120 may pass only a signal existing in a frequency within a specific range through band filtering, remove signals beyond the specific range, and output the signal within the specific range. According to an embodiment, an example of the result (for example, pre-processed PPG signal) of pre-processing the input signal (for example, the PPG signal) through a pre-processing operation 1120 is illustrated in FIG. 12B.

Figure 12C:
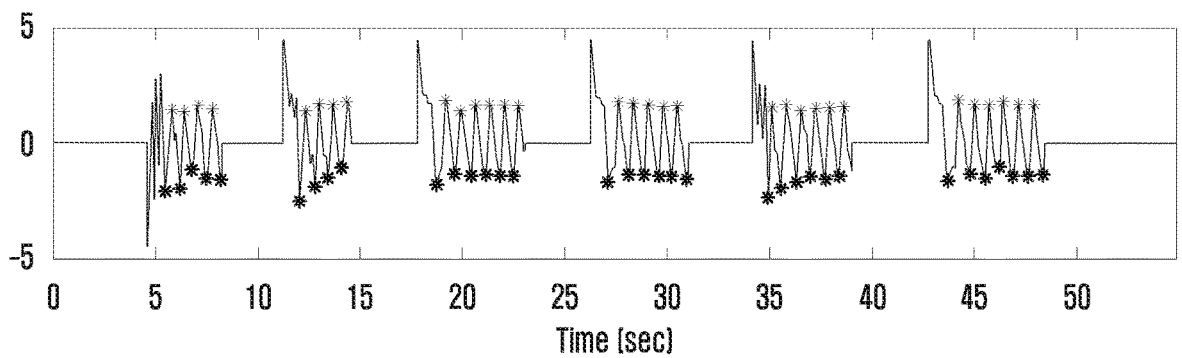

In operation 1130, the processor 120 may segment the pre-processed signal (for example, a pre-processed PPG signal). According to an embodiment, a segmentation operation 1130 may include a key point detection operation 1131. According to an embodiment, a key point of the waveform may include a peak, a valley, or an inflection point. According to an embodiment, the key point detection operation 1131 may detect a temporal peak value in the pre-processed signal. For example, the processor 120 may detect a peak in the waveform according to the pre-processed signal so as to detect a heartbeat point, and may calculate a time interval from an immediately preceding heartbeat whenever a heartbeat is generated. According to an embodiment, an example of the result of segmentation of the pre-processing signal (for example, a segmented PPG signal) through a key point detection operation 1131 is illustrated in FIG. 12C.

Figure 12D:
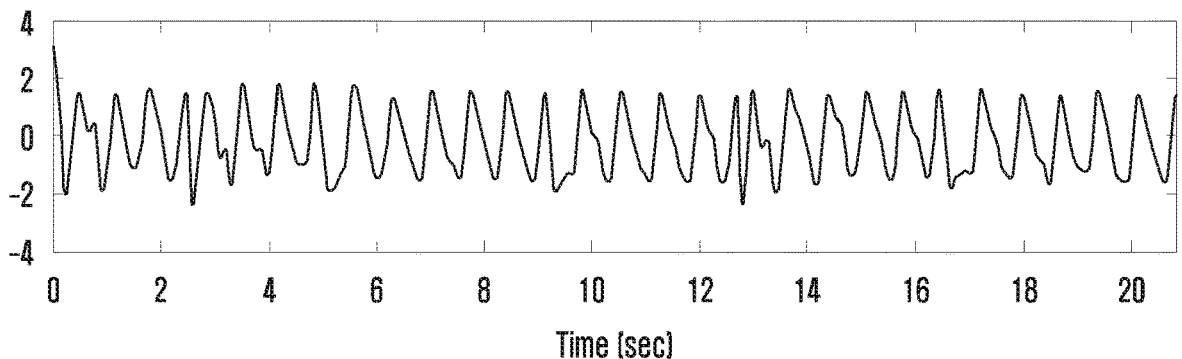

In operation 1140, the processor 120 may merge segmented signals (for example, segmented PPG signals). According to an embodiment, the merging operation 1140 may include a similarity check and validation operation 1141. According to an embodiment, the similarity check and validation operation 1141 may include an operation of checking and validating the similarity between segmented signals (for example, a set of multiple PPG signals). According to an embodiment, when the similarity between a first segmentation signal and a second segmentation signal is not validated, the first segmentation signal may be excluded, and the similarity between the second segmentation signal and a third segmentation signal may be determined. According to an embodiment, an example of the result of merging segmented signals for discontinuous measurement data is illustrated in FIG. 12D.

Figure 13:
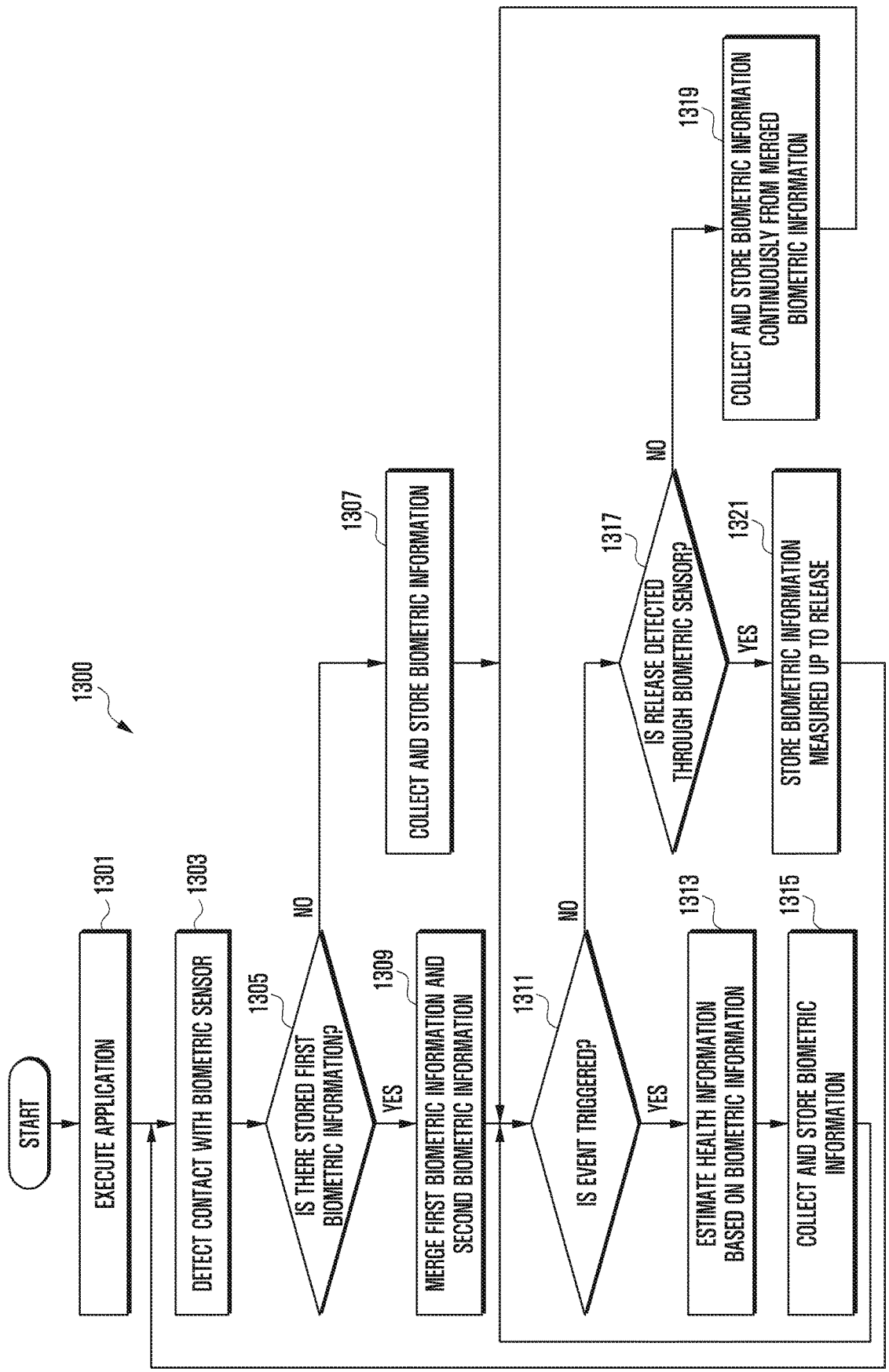
FIG. 13 is a flowchart illustrating a method by which an electronic device processes discontinuous measurement data according to various embodiments.

FIG. 13 is a flowchart 1300 illustrating a method by which an electronic device processes discontinuous measurement data according to various embodiments.

Referring to FIG. 13, in operation 1301, the processor 120 of the electronic device 101 (or the function-processing module 500 of FIG. 5) may execute an application. According to an embodiment, the user may input an execution command (for example, may touch an application icon) for executing the corresponding application to perform a function such as a call or photography (for example, selfie), and the processor 120 may execute the application on the basis of the execution command. According to an embodiment, operation 1301 may include a state in which the application is initially executed or a state in which the application is being executed.

In operation 1303, the processor 120 may detect contact with (attachment to) an external object (for example, a user's finger) through a biometric sensor. According to an embodiment, the user may bring his/her finger into contact with the biometric sensor while the application executed through the electronic device 101 is used (for example, use related to a selfie or use related to a call). The processor 120 may determine whether an input signal (for example, a PPG signal input) corresponding to biometric information is detected by monitoring the biometric sensor while the application is executed.

In operation 1305, the processor 120 may determine whether there is previously stored biometric information (hereinafter, referred to as "first biometric information" in FIG. 13) in response to detection of contact with the biometric sensor. According to an embodiment, the processor 120 may store biometric information (for example, a raw PPG signal) measured (or collected) on the basis of the biometric sensor in a memory (for example, the memory 130 of FIG. 1). When the contact with the biometric sensor is detected, the processor 120 may determine whether there is first biometric information by referring to the memory 130. According to an embodiment, the first biometric information may be information stored at the time point at which measurement of biometric information by the biometric sensor is stopped (for example, the time point at which the finger in contact with the biometric sensor is removed therefrom).

According to various embodiments, the first biometric information may be managed on the basis of at least an elapsed time or a state change in the electronic device 101 (or user) (for example, a change in at least one of momentum or location). According to an embodiment, the first biometric information may be information included in a first range (for example, a predetermined time, such as 3 seconds, 5 seconds, 1 minute, 10 minutes, 30 minutes, 1 hour, or 1 day) configured on the basis of the current time. For example, when the configured range is 1 minute, the first biometric information is information obtained 10 minutes before the time point at which operation 1305 is performed, and information obtained after 1 minute is not included in the first biometric information. According to an embodiment, the first biometric information may be information included within a second range, in which the state change in the electronic device 101 is configured. For example, previously measured biometric information A and currently measured biometric information B may be completely different from each other according to a user's motion state (or movement state). For example, biometric information A is information when the user is in motion and biometric information B is information when the user is not in motion. In the opposite case, the nature of biometric information (for example, waveform of the PPG signal) may be completely different. As described above, when the state change in the electronic device 101 exceeds the configured range (for example, when the state change exceeds a configured reference change), the information may be excluded from the first biometric information.

According to various embodiments, the state change in the electronic device 101 may be determined on the basis of at least context awareness or various pieces of measurement information related to the user, managed by a health care application. According to various embodiments, whether to use the first biometric information may be determined in consideration of both the first range and the second range. According to various embodiments, in connection with the first biometric information, the first biometric information may be validated on the basis of at least one reference range such as the first range or the second range, and the first biometric information may be used to merge discontinuous measurement data when the first biometric information is information within the reference range on the basis of at least the validation result. This is to prevent inaccurate health information estimation (or serving of erroneous data) due to the use of first biometric information completely different from the currently measured biometric information.

When there is no first biometric information in operation 1305 (No in operation 1305), the processor 120 may perform an operation of collecting and storing biometric information on the basis of the biometric sensor in operation 1307. The processor 120 may perform operation 1307 and operation 1311 sequentially or in parallel.

When there is the first biometric information in operation 1305 (Yes in operation 1305), the processor 120 may merge the first biometric information with currently measured biometric information (hereinafter, referred to as "second biometric information" in FIG. 13). According to an embodiment, merging of the first biometric information and the second biometric information may correspond to the description made with reference to FIGS. 11 and 12. According to an embodiment, the processor 120 may continuously collect and store biometric information on the basis of the biometric sensor, sequentially or in parallel with merging discontinuous measurement data such as the first biometric information and the second biometric information. According to an embodiment, the processor 120 may validate the first biometric information on the basis of at least the first range or the second range in operation 1309, and when it is determined that the first biometric information is not valid, may perform operation 1307 even though the first biometric information exists.

In operation 1311, the processor 120 may determine whether an event is triggered sequentially or in parallel with operation 1307 or operation 1309. According to an embodiment, the processor 120 may determine whether an event related to health information (for example, heart-rate information) is generated. For example, the processor 120 may determine whether biometric information through which health information can be estimated is accumulated.

When the event is triggered in operation 1311 (Yes in operation 1311), the processor 120 may estimate health information on the basis of biometric information. According to an embodiment, the processor 120 may perform an operation of post-processing the estimated health information and providing the health information through the display device 160.

The processor 120 may continuously collect and store biometric information sequentially or in parallel with operation 1313 in operation 1315, or may perform an operation related to estimation of other health information in operation 1311. The processor 120 may perform operations 1311 to 1315 until execution of the application ends or removal of the user's finger from the biometric sensor is detected.

When the event is not triggered in operation 1311 (No in operation 1311), the processor 120 may determine whether an external object (for example, a user's finger) is removed (detached) through the biometric sensor in operation 1317. For example, the processor 120 may determine whether the contacting user's finger is removed in operation 1303.

When removal thereof is not detected (or when the contact is maintained) in operation 1317 (No in operation 1317), the processor 120 may collect and store biometric information continuously with merged biometric information obtained by merging the first biometric information and the second biometric information in operation 1319. According to an embodiment, the processor 120 may determine a trigger according to operation 1311 or operation 1317 while performing operation 1319 sequentially or in parallel with operation 1309.

When removal thereof is detected in operation 1317 (Yes in operation 1317), the processor 120 may store measured biometric information until removal is detected in operation 1321. According to an embodiment, the measured biometric information may include merged biometric information, and may include collected biometric information continuously with the merged biometric information until the removal. According to an embodiment, the processor 120 may proceed to operation 1303 after operation 1321 and perform operations following operation 1303.

Figure 14:
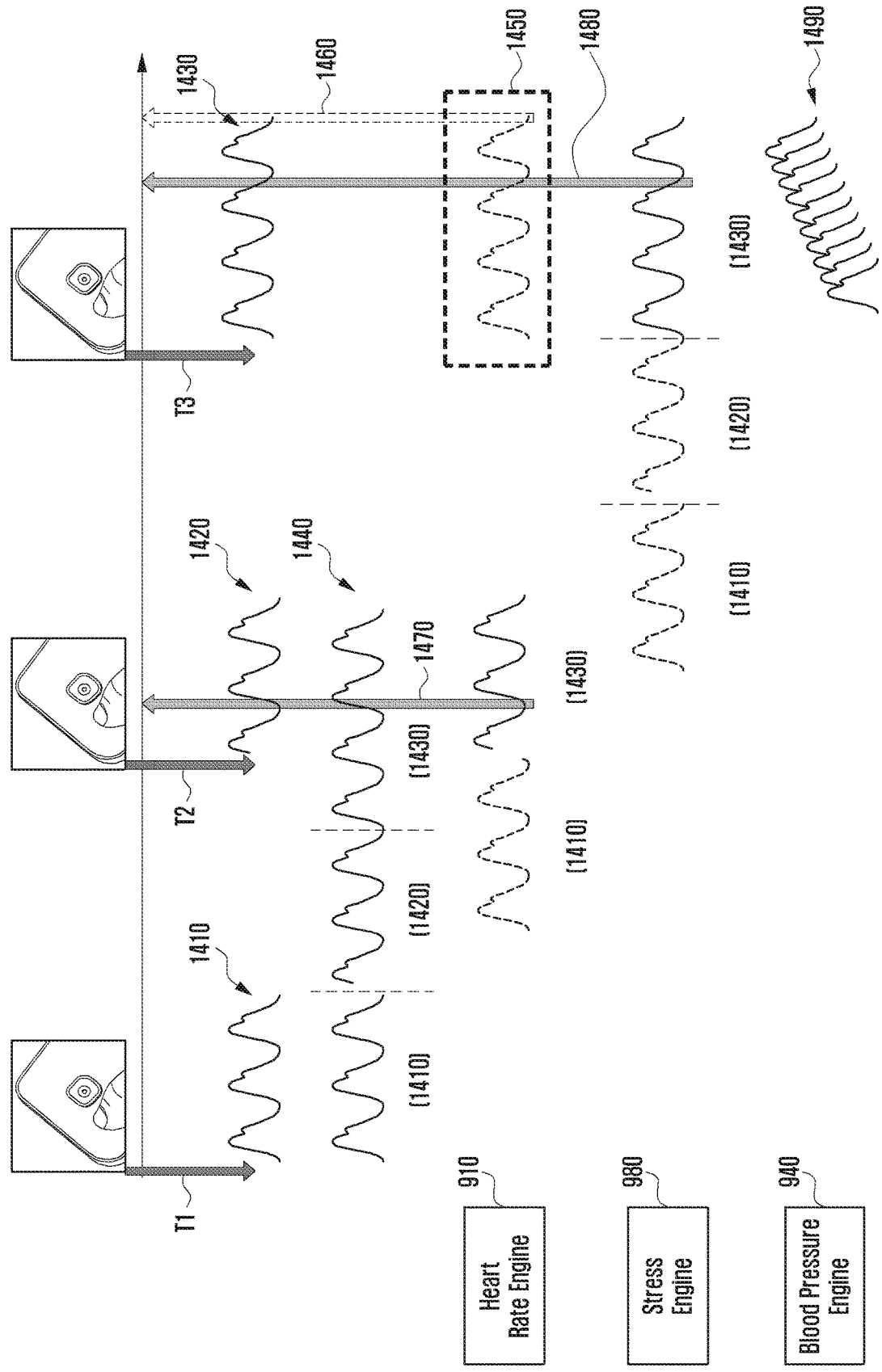
FIGS. 14A, 14B, and 14C illustrate an example in which an electronic device merges discontinuous measurement data according to various embodiments.

FIG. 14 illustrates an example in which an electronic device merges discontinuous measurement data according to various embodiments.

As illustrated in FIG. 14, FIG. 14 illustrates an example in which the electronic device 101 repeatedly brings the finger into contact with the biometric sensor and removes the finger from the biometric sensor, and merges discontinuous measurement data measured in every contact (attach) session (or for a short time interval (for example, about 3 to 5 seconds)) while the application is being executed. According to various embodiments, one set of continuously measured data may be configured through merging of discontinuous measurement data.

FIGS. 14A, 14B, and 14C illustrate attach sessions (or contact sections) in which the user brings a finger into contact with the biometric sensor of the electronic device 101. Between FIGS. 14A and 14B and between FIGS. 14B and 14C, a release (detach) session (or a release section) in which the user removes the finger from the biometric sensor of the electronic device 101, is shown. For example, the user may repeat the contact and release such that the user makes finger contact and releases the finger contact after a first predetermined time (for example, about 2 to 5 seconds) in FIG. 14A and makes finger contact and releases the finger contact after a second predetermined time (for example, about 2 to 5 seconds) in FIG. 14B.

According to various embodiments, the electronic device 101 may recognize the contact session through the biometric sensor in FIGS. 14A, 14B, and 14C. The electronic device 101 may measure biometric information 1410, 1420, and 1430 (hereinafter, referred to as "measurement data" in FIG. 14) corresponding to contact sessions from the time point at which the contact session starts (or the time point at which an event is generated) (for example, a first time T1, a second time T2, or a third time T3) to the time point at which the contact session ends. According to an embodiment, the electronic device 101 may acquire first measurement data 1410 during a first contact session according to FIG. 14A, acquire second measurement data 1420 during a second contact session according to FIG. 14B, and acquire third measurement data 1430 during a third contact session according to FIG. 14C on the basis of a biometric signal (for example, a PPG signal) measured by the biometric sensor (for example, a PPG sensor).

According to various embodiments, the electronic device 101 may merge discontinuous measurement data related to biometric information, such as the first measurement data 1410, the second measurement data 1420, and the third measurement data 1430, acquired during the first contact session (FIG. 14A), the second contact session (FIG. 14B), and the third contact session (FIG. 14C). According to an embodiment, when a biometric signal is detected at the second time T2 of the second contact session in the state in which the first measurement data 1410 acquired in the first contact session is stored, the electronic device 101 may merge the first measurement data 1410 and the second measurement data 1420 detected during the second contact session. For example, the electronic device 101 may store and manage one set of measurement data (or biometric information) by merging the first measurement data 1410 and the second measurement data 1420 when the second contact session expires. Through the operation, the electronic device 101 may merge the discontinuous measurement data (for example, the first measurement data 1410, the second measurement data 1420, and the third measurement data 1430) corresponding to the first contact session, the second contact session, and the third contact session into one set of measurement data 1440 (or biometric information). According to various embodiments, the electronic device 101 may estimate health information on the basis of the merged measurement data.

According to an embodiment, it may be assumed that the first measurement data 1410 of the first contact session and the second measurement data 1420 of the second contact session are not included in a condition (for example, measurement time or number of measurements) required for estimation of the first health information (for example, heart-rate information), and that the third measurement data 1430 of the third contact session is included in the condition required for estimation of the first health information (for example, heart-rate information). The first health information (for example, the heart-rate information) may not be estimated based on the first measurement data 1410 and the second measurement data 1420, which are independent in the first contact session and the second contact session, and the first health information (for example, heart-rate information) may be estimated by the third measurement data 1430 of the third contact session. Accordingly, when the states of FIGS. 14A, 14B, and 14C are repeated while the electronic device 101 executes an application, the first health information (for example, heart-rate information) may be estimated at an $N^{th}$ time 1460 on the basis of the third measurement data 1430 of the third contact session of FIG. 14C, as actually indicated by element 1450 in the prior art.

According to various embodiments, the electronic device 101 may estimate the first health information (for example, heart-rate information) at an $M^{th}$ time 1470 on the basis of merged data obtained by merging the first measurement data 1410 of the first contact session in FIG. 14A and the second measurement data 1420 of the second contact session in FIG. 14B. For example, the heart rate engine 910 may generate an event related to the first health information at the $M^{th}$ time 1470, earlier than the $N^{th}$ time 1460. For example, the electronic device 101 may estimate the first health information during the second contact session in FIG. 14B and provide the first health information to the user.

According to an embodiment, the first measurement data 1410 of the first contact session, the second measurement data 1420 of the second contact session, and the third measurement data 1430 of the third contact session may not be included in a condition required for estimation of second health information (for example, stress information) having more requirements (for example, measurement time or number of measurements) than the first health information (for example, heart-rate information). Accordingly, when the states of FIGS. 14A, 14B, and 14C are repeated while the electronic device 101 executes the application, the second health information (for example, stress information) may not be estimated during the contact sessions of FIGS. 14A, 14B, and 14C in the prior art.

According to various embodiments, the electronic device 101 may estimate the second health information (for example, stress information) at an $X^{th}$ time 1480 on the basis of merged data, obtained by merging the first measurement data 1410 of the first contact session of FIG. 14A, the second measurement data 1420 of the second contact session of FIG. 14B, and the third measurement data 1430 of the third contact session of FIG. 14C. For example, the stress engine 980 may generate an event related to the second health information at the $X^{th}$ time 1480. For example, the electronic device 101 may estimate the second health information during the third contact session of FIG. 14C and provide the second health information to the user.

According to an embodiment, it may be difficult to provide reliable third health information (for example, a blood pressure measurement value) before a predetermined number of waveforms or more is extracted in analysis of the third health information (for example, blood pressure information) based on waveform analysis. For example, the blood pressure measurement may be performed according to a method requiring one complete (or clean (for example, having no noise)) waveform, but the complete waveform may not be acquired at one time depending on the measurement situation. For example, when the complete waveform is not capable of being determined based on each of the first measurement data 1410 of the first contact session, the second measurement data 1420 of the second contact session, and the third measurement data 1430 of the third contact session, the complete waveform (having, for example, a signal capable of being used to calculate blood pressure and including no noise) that meets a condition required for estimation of the third health information (for example, blood pressure information) may not be extracted.

According to various embodiments, the electronic device 101 may acquire and analyze a plurality of waveforms on the basis of merged data (for example, an element 1490) obtained by merging the first measurement data 1410 of the first contact session of FIG. 14A, the second measurement data 1420 of the second contact session of FIG. 14B, and the third measurement data 1430 of the third contact session of FIG. 14C. According to an embodiment, it may be more important for the third health information (for example, blood pressure information) based on waveform analysis to extract one complete waveform (having, for example, a signal for calculating blood pressure and including no noise) that meets a condition, rather than the number of waveforms. According to various embodiments, it is possible to estimate reliable third health information (for example, blood pressure information) by extracting the complete waveform from the merged data 1490, obtained by merging a predetermined number of waveforms. For example, the blood pressure engine 940 may find a waveform that is easily calculated from a plurality of waveforms 1490 of the merged data 1490 compared to an individual waveform, overlap waveforms to a level at which calculation is easy (ensemble average), or extract a complete waveform by excluding waveforms containing noise, and estimate third health information (for example, blood pressure information) from the extracted complete waveform and provide the third health information to the user. According to an embodiment, an example of the merged data 1490 may be an example of overlapping to facilitate calculation of waveforms corresponding to the first measurement data 1410, the second measurement data 1420, and the third measurement data 1430.

As illustrated in the example with reference to FIG. 14, the electronic device 101 may merge discontinuous measurement data over time. According to various embodiments, as the amount of merged data based on discontinuous measurement data increases, the number of pieces of biometric information that can be acquired (or estimated) substantially in proportion to the merged data may be augmented. According to various embodiments, it is possible to acquire biometric information requiring long continuous measurement through merging of discontinuous measurement data in a short time. According to various embodiments, more realistic emotion information may be provided by merging image information based on images (for example, selfie images) acquired from an image sensor (for example, a camera) in addition to biometric information acquired from the biometric sensor.

According to various embodiments, as illustrated in FIG. 14, an initial measurement time of the biometric information may be reduced using pre-stored biometric information. According to an embodiment, in the case of biometric information having a relatively long measurement time (for example, having a larger number of sample pulse waves), a plurality of waveforms may be generally continuously acquired and analyzed within the same environment. According to an embodiment, in the case of stress, the minimum number of samples (for example, at least three samples) may be basically required by determining the peak time of the waveform rather than the shape of the waveform. For example, when measurement is not continuously performed for a predetermined time in the conventional initial stress measurement operation, it is difficult to derive a measurement value. According to various embodiments, even though the number of samples required for each contact session is not satisfied, it is possible to reduce the amount of time required for measurement by rapidly satisfying the minimum number of samples required by merged data.

According to an embodiment, in the case of blood pressure, one complete waveform may be required, rather than a number of samples for determining the waveform. Accordingly, in the case of blood pressure, while measurement can be performed through only one waveform, measurement may not be performed in the case of a waveform that is not complete. For example, it may be required to provide a reliable blood pressure value on the basis of a predetermined number of waveforms or more even in blood pressure analysis based on waveform analysis. According to various embodiments, it is possible to reduce uncertainty and increase reliability of the measurement value that is generated when the waveform in one period is analyzed on the basis of merged data. For example, for blood pressure, a predetermined number of waveforms is not important, but extraction of a complete waveform (for example, having a signal capable of being used to calculate blood pressure and including no noise) that meets a condition may be important. According to various embodiments, a waveform that can be easily calculated may be more rapidly found on the basis of merged data. According to various embodiments, it may be possible to derive the complete waveform based on merged data (for example, overlapping waveforms) even if there is no complete waveform among individual waveforms.

According to various embodiments, in an unconscious measurement operation scenario, it is preferable to merge (or combine) discontinuous measurement data at the moment the signal is measured by the sensor than to induce the user to intentionally and continuously perform measurement through the sensor for a long time so as to acquire and analyze a plurality of waveforms. According to an embodiment, it is possible to analyze a plurality of discontinuous waveforms acquired in the same environment and operation within a short time and merge discontinuous waveforms, which are more similar than pre-acquired waveforms, and the merged waveforms may be generated as one continuously acquired signal. According to an embodiment, when biometric information is measured on the basis of the merged signal, the reliability of the measurement value may be maintained and the time required for measurement may be reduced.

According to an embodiment, the user may continuously and repeatedly bring his/her finger into contact with the sensor of the electronic device 101 (attached state) and remove his/her finger from the sensor (detached state) while using the selfie mode. In this case, in the conventional continuous measurement scenarios, biometric information that requires a plurality of measurement waveforms for a long time, such as stress information or blood pressure information, may not be acquired. Further, biometric information of the user collected for a short time may not change much and may thus have sufficient similarity, and even discontinuously measured signals may differ little from continuously acquired signals. In a scenario according to various embodiments, as the user repeatedly brings his/her finger into contact with the sensor and removes his/her finger from the sensor while using the selfie mode, stress information or blood pressure information may be continuously provided from an arbitrary starting point. That is, according to various embodiments, stress information or blood pressure information may be immediately acquired even if the user brings his/her finger into contact with the sensor only for a short time from an arbitrary starting point (for example, after a condition required for measurement is satisfied, since discontinuous measurement data are merged).

According to various embodiments, in merging discontinuous data, measurement data (or a waveform) corresponding to a predetermined condition may be excluded from targets to be measured. For example, in cases in which a measurement time is short and thus a minimum number of waveforms is not obtained during contact sessions, such as cases in which waveforms include a lot of noise (for example, operating noise is generated), a contact session is created after a predetermined time from a previous contact session (for example, the time difference between a first contact session and a second contact session is large), the target to be measured is changed, the external environment (for example, temperature or humidity) is significantly changed, a sensor state error is detected, or a user biometric change is detected (owing, for example, to weight or exercise), may be excluded from merging of the corresponding measurement data (or waveforms or signals).

Figure 15:
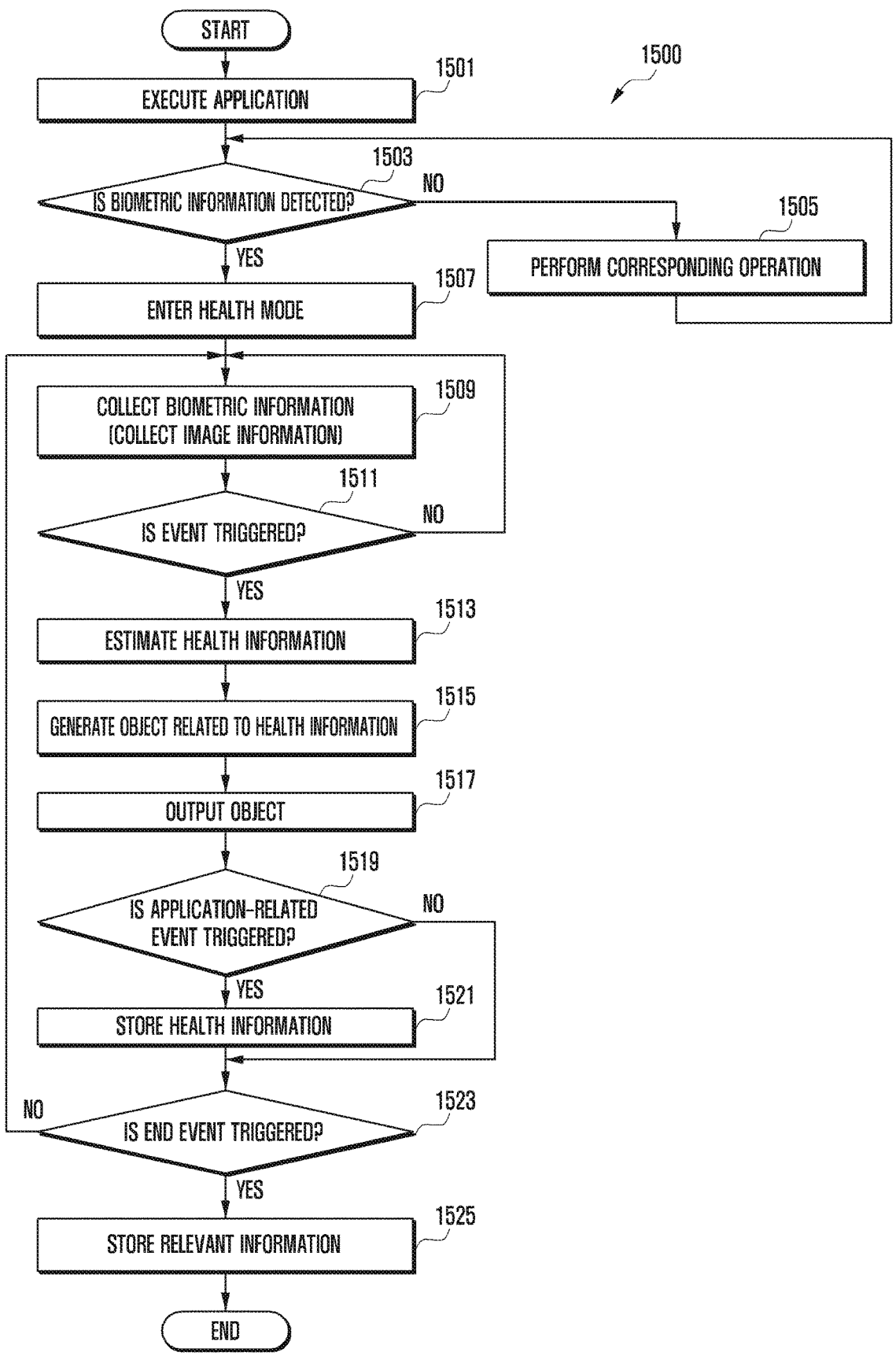
FIG. 15 is a flowchart illustrating a method of operating an electronic device according to various embodiments.

FIG. 15 is a flowchart 1500 illustrating a method of operating an electronic device according to various embodiments.

As illustrated in FIG. 15, FIG. 15 illustrates a scenario in which the electronic device 101 measures biometric information while an application (for example, a selfie mode) is executed, and provides relevant health information to the user.

Referring to FIG. 15, in operation 1501, the processor 120 of the electronic device 101 (or the function-processing module 500 of FIG. 5) may execute the application. According to an embodiment, the user may select a camera application for a selfie, and the processor 120 may enter the selfie mode in response to detection of selection of the camera application. According to an embodiment, the processor 120 may display a screen including a selfie image (for example, a user image) through the display device 160 in response to entry into the selfie mode.

In operation 1503, the processor 120 may determine whether biometric information is detected by a biometric sensor. According to an embodiment, the processor 120 may monitor the biometric sensor and determine whether an input signal (for example, a PPG signal input) corresponding to biometric information is detected based on contact with an external object (for example, a user's finger) through the biometric sensor.

When there is no detection of biometric information through the biometric sensor in operation 1503 (No in operation 1503), the processor 120 may perform operation 1505. According to an embodiment, the processor 120 may perform the operation corresponding to a user's request related to a function of the application. For example, the processor 120 may perform an operation of capturing and storing a selfie image in response to a capture request from the user while displaying a preview screen in the selfie mode. According to an embodiment, the processor 120 may perform operation 1503 in parallel with the corresponding operation until execution of the application ends.

When biometric information is detected through the biometric sensor in operation 1503 (Yes in operation 1503), the processor 120 may enter a health mode in operation 1507. According to an embodiment, the processor 120 may execute the health mode (for example, a second operation mode) in parallel while maintaining the executed selfie mode (for example, a first operation mode). According to an embodiment, the first operation mode is a mode corresponding to the executed application, and may be performed as a foreground operation. According to an embodiment, the second operation mode is a mode (for example, a vision health mode) for unconsciously measuring biometric information according to various embodiments separately from the executed application and visually providing relevant health information, and may be performed as a background operation. According to an embodiment, the processor 120 may provide the result of the second operation mode, performed as the background operation, on a screen of the first operation mode, performed as the foreground operation. According to an embodiment, the second operation mode (for example, the health mode) may be performed while contact between the biometric sensor and the user's finger is maintained while the application is executed. For example, the second operation mode may be activated during contact between the biometric sensor and the user's finger, and may be deactivated while the user's finger is removed from the biometric sensor, and activation and deactivation may be toggled according to repetition between the contact and the removal.

In operation 1509, the processor 120 may collect biometric information on the basis of the biometric sensor. According to an embodiment, the processor 120 may acquire image information (for example, a user's selfie image) on the basis of the image sensor, sequentially or in parallel with collection of the biometric information. According to an embodiment, the collected biometric information may include currently measured biometric information and previously collected and stored biometric information.

In operation 1511, the processor 120 may determine whether an event is triggered. According to an embodiment, the processor 120 may determine whether health information can be estimated on the basis of the collected biometric information. For example, the processor 120 may generate an event in response to collection of biometric information through which the health information can be estimated.

When no event is triggered in operation 1511 (No in operation 1511), the processor 120 may proceed to operation 1509 and perform operations following operation 1509. According to an embodiment, when an event is not triggered while biometric information is collected, the processor 120 may perform an operation of determining whether the health mode is released, for example, whether contact from the biometric sensor is released in parallel.

When an event is triggered in operation 1511 (Yes in operation 1511), the processor 120 may estimate health information on the basis of biometric information in operation 1513. According to an embodiment, the processor 120 may estimate a plurality of pieces of health information that can be estimated on the basis of the measured biometric information, and may sequentially estimate additional health information on the basis of biometric information, the amount of which increases over time. According to an embodiment, when emotion information can be estimated on the basis of the increased amount of biometric information, the processor 120 may express more intuitive and realistic emotion information by merging image information acquired by the image sensor. According to various embodiments, expression of the emotion information will be described with reference to the drawings below.

In operation 1515, the processor 120 may generate a visual object (or item) related to health information. According to an embodiment, the processor 120 may perform post-processing to provide (or display) at least one piece of estimated health information to the user. For example, the processor 120 may generate a relevant object (for example, text, a number, an icon, a graph, a waveform, or an emotion) for visually expressing health information in connection with the application executing the estimated health information.

In operation 1517, the processor 120 may output the object. According to an embodiment, the processor 120 may select an area to display an object of health information on the screen of the display device 150 and display the relevant object in the selected area. According to an embodiment, the processor 120 may determine an area in which to display the object in connection with the executed application. For example, the processor 120 may identify a screen configuration of the application and select an area which does not influence the executed application in the screen configuration (or which does not hide the screen), or may select a predetermined area (for example, a user face area) according to the type of health information (or the type of object). According to various embodiments, when providing the object related to the health information, the processor 120 may augment and display the object over time. According to various embodiments, providing the object related to the health information will be described with reference to the drawings below.

In operation 1519, the processor 120 may determine whether an application-related event is triggered. According to an embodiment, the application-related event may include, for example, a photography command input by the user in the selfie mode or a health information transmission command input by the user in the call mode (for example, a voice call or video call mode). According to an embodiment, the application-related event may include input for storing health information.

When no application-related event is triggered in operation 1519 (No in operation 1519), the processor 120 may proceed to operation 1523 and perform operations following operation 1523.

When an application-related event is triggered in operation 1519 (Yes in operation 1519), the processor 120 may store health information in operation 1521. According to an embodiment, the processor 120 may generate content (for example, a selfie image) on the basis of a photography command in the selfie mode, associate (or map) meta information of the content (for example, a content name, a creation location, a creation time, a storage address, or a content format) with health information, and store the same. According to an embodiment, the processor 120 may generate content (for example, a message) on the basis of a transmission command in the call mode, associate (or map) meta information of the content (for example, a message format, a reception number, a transmission number, a message title, or attachments), and store the same. According to an embodiment, in the call mode, the processor 120 may further perform an operation of transmitting a message including health information (for example, text-based or image-based information) to a counterpart electronic device in the call mode.

In operation 1523, the processor 120 may determine whether execution of the application ends. According to an embodiment, the processor 120 may determine whether a request for ending the executed application is made by the user (in, for example, the selfie mode or the call mode) or originates externally (in, for example, the call mode).

In operation 1523, the processor 120 may determine whether an end event is triggered. According to an embodiment, when execution of the application ends (for example, when the selfie mode ends) or when the user's finger is removed from the biometric sensor (for example, when the health mode ends), the end event may be triggered.

When the end event is not triggered in operation 1523 (No in operation 1523), the processor 120 may proceed to operation 1509 and perform operations following operation 1509.

When the end event is triggered in operation 1523 (Yes in operation 1523), the processor 120 may store relevant information in operation 1525. According to an embodiment, the processor 120 may store biometric information measured until a time point at which the end event is triggered in response to the end event. According to an embodiment, when storing biometric information, the processor 120 may map information on a time (a time stamp) at which the biometric information is stored (or generated) to the biometric information and store the same.

FIG. 16 illustrates an example of an operation scenario in which an electronic device provides health information to the user according to various embodiments.

Figures 16A, 16B, 16C, 16D, 16E:
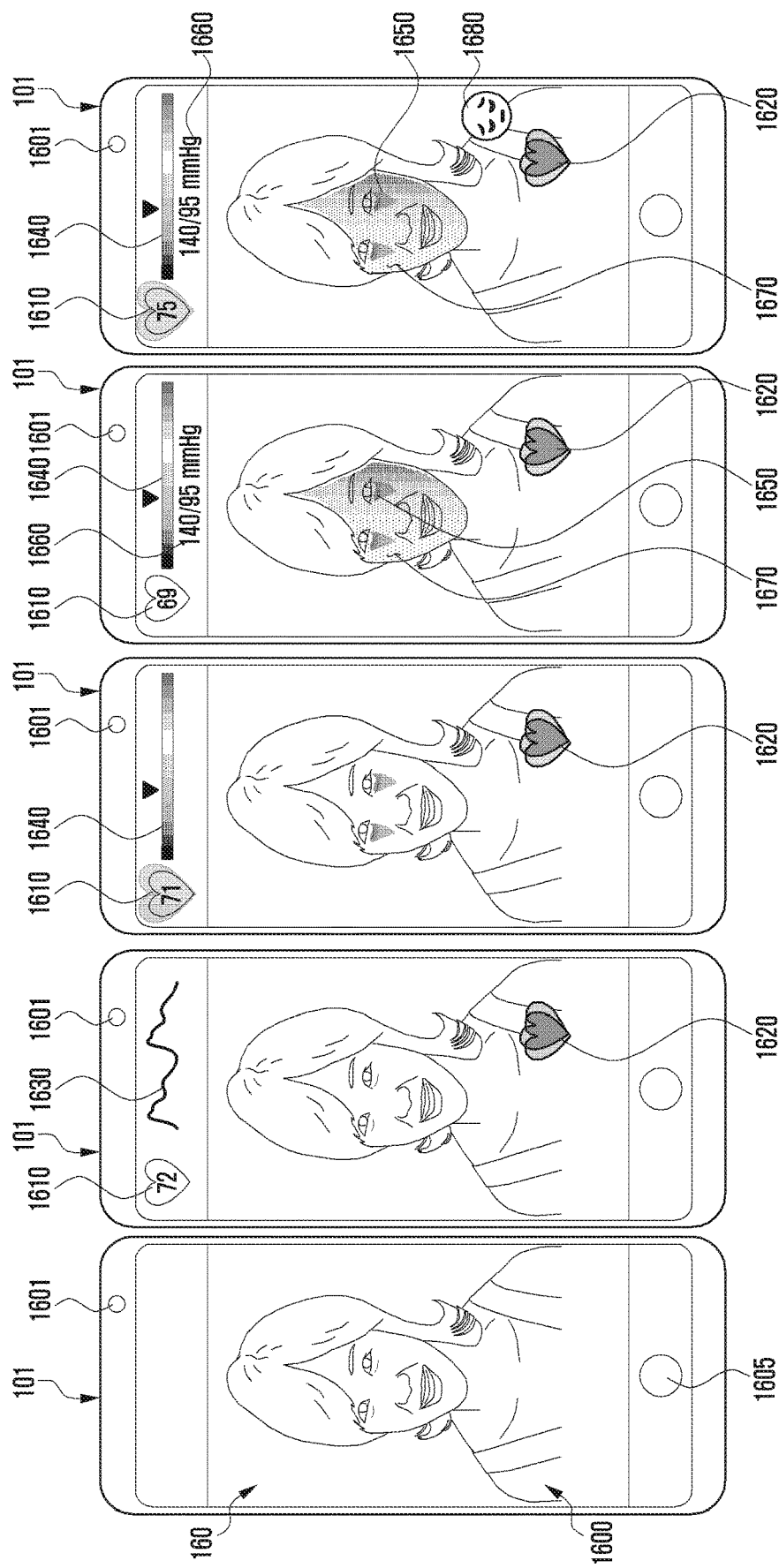
FIGS. 16A, 16B, 16C, 16D, and 16E illustrate an example of an operation scenario in which an electronic device provides health information to the user according to various embodiments.

As illustrated in FIG. 16, FIG. 16 illustrates an operation example in which the electronic device 101 provides health information related to the user while a selfie mode is executed. According to an embodiment, FIGS. 16A to 16E illustrate examples over time (or according to a biometric information measurement time).

Referring to FIG. 16, the electronic device 101 may enter a selfie mode and display an execution screen related to the selfie mode through the display device 160 in FIG. 16A. According to an embodiment, the execution screen may include a user image 1600 (for example, a selfie image) acquired through a front camera 1601 and a photographing button 1605 for receiving a photography request from the user.

According to various embodiments, as illustrated in FIG. 7A, the user may bring his/her finger into contact with the sensor 710 disposed on the rear surface of the electronic device 101 while using the selfie mode. According to various embodiments, the electronic device 101 may monitor whether the user's finger contacts the sensor 710 while the selfie mode is executed, and, when contact with the sensor 710 is detected, may collect biometric information. According to an embodiment, the electronic device 101 may enter a health mode in response to detection of the contact with the sensor 710 while the selfie mode is executed and continuously collect (or measure) a user's biometric information over time. According to an embodiment, the electronic device 101 may collect a sensor measurement value (that is, biometric information) by the sensor 710 and image information captured through a front camera 1601 while a contact session of the health mode is maintained in the state in which the finger is located on the sensor 710. According to an embodiment, the electronic device 101 may calculate a measurement time up to the current time (for example, a condition for estimating health information) through a timer counter (not shown) and estimate health information that can be used (or estimated) on the basis of the measurement time.

According to various embodiments, the electronic device 101 may provide the estimated health information to the user on the basis of a relevant object. According to an embodiment, the electronic device 101 may estimate at least one piece of health information on the basis of biometric information acquired (or accumulated) over time, and may additionally display estimated (or updated) health information, or may augment and display the health information on the conventional health information.

According to an embodiment, in FIG. 16B, the electronic device 101 may provide at least one object (for example, at least one of a first object 1610, a second object 1620, or a third object 1630) related to first health information (for example, heart-rate information). For example, the first object 1610 may be an example of expression of heart-rate information in the form of an icon including numerical data, the second object 1620 may be an example of expression of heart-rate information (or heart-rate variability) in the form of a schematic waveform, and the third object 1630 may be an example of expression of a heartbeat in a user image (for example, near a user's heart) on the basis of a graphic effect (or an animation effect). According to various embodiments, the electronic device 101 may sequentially or in parallel estimate at least one piece of second health information (for example, oxygen saturation and heart-rate variability) having substantially the same (or similar) measurement time as (or to) first health information and provide an object related to the first health information and an object related to the second health information together.

According to various embodiments, the electronic device 101 may augment and display health information on the basis of biometric information estimated over time, and may additionally display additional health information or replace the conventional health information with the additional health information.

According to an embodiment, in FIGS. 16C, 16D, and 16E, when the first health information (for example, heart-rate information) is updated, the electronic device 101 may augment and display at least one object related to the first health information. For example, the first object 1610 may be displayed after being changed to updated numerical data (for example, 72->71->69->75).

According to an embodiment, in FIG. 16C, when an event for third health information (for example, stress information) is generated according to the measurement level of biometric information, the electronic device 101 may add at least one object (for example, a fourth object 1640 and a fifth object 1650) related to the third health information (for example, stress information) as well as the existing first health information (for example, heart-rate information) on the screen, or may replace the existing object with the at least one object. According to an embodiment, the electronic device 101 may replace the third object 1630, indicating a stress index, with the fourth object 1640 in a display area of the existing third object 1630, and may overlay (or augment) and display the fifth object 1650 (for example, the graphic effect) corresponding to the stress index on a user image 1600.

According to an embodiment, in FIGS. 16D and 16E, when an event for fourth health information (for example, blood pressure information) is generated according to a measurement level of biometric information, the electronic device 101 may add at least one object (for example, a sixth object 1660 and a seventh object 1670) related to the fourth health information (for example, blood pressure information) as well as the existing health information (for example, heart-rate information and stress information) on the screen, or may replace the existing objects with the at least one object. According to an embodiment, the electronic device 101 may display the sixth object 1660, indicating a blood pressure level (for example, 140/95 mmHg), in a configured area, and may overlay (or augment) and display the seventh object 1670 (for example, the color of a user's face, corresponding to blood pressure) corresponding to the blood pressure level on the user image 1600 (for example, the face area). For example, the electronic device 101 may change the face color according to the blood pressure level so as to intuitively display an increase or decrease in the user's blood pressure.

According to an embodiment, in FIG. 16E, when an event for fifth health information (for example, emotion information) is generated according to a measurement level of biometric information, the electronic device 101 may add at least one object (for example, an eighth object 1680) of the fifth health information (for example, emotion information) as well as the existing health information (for example, heart-rate information, stress information, and blood pressure information) on the screen, or may replace the existing objects with the at least one object. According to an embodiment, the electronic device 101 may overlay (or augment) and display a graphic object such as an avatar or an emotional emoticon (or Emoji) on the user image 1600.

According to various embodiments, as illustrated in FIG. 16, various effects may be designated on the basis of biometric information to allow the user to intuitively know the user's state through the application of a graphic effect or an animation effect, instead of a detailed measurement value for user's biometric information.

According to various embodiments, the electronic device 101 may perform processing using an image (image processing) in connection with augmenting and displaying health information (or an object related to health information) on the screen. According to an embodiment, in order to select an area to display at least one object related to health information, the electronic device 101 may perform processing based at least on extraction of feature points from the user image, face recognition (or facial recognition), and learning (for example, machine learning). According to an embodiment, the electronic device 101 may select a preconfigured area according to an object (or health information) and a body region (for example, near the heart, near the eyes, or in a face area) according to processing, and display the corresponding object in the selected area.

For example, the electronic device 101 may use an augmented-reality (AR) scheme for expressing virtual-reality (VR) data (for example, an object) in real time on an image (for example, a preview image) acquired through a camera. According to an embodiment, it is possible to estimate an image form and location from the image, select an area to express collected biometric information, and then apply post-processing based on biometric information to the corresponding area. For example, the post-processing may include provision of new text or images, a change in an object color or form, and a change in a background color or form. According to various embodiments, the post-processed image (for example, the object and the user image) may be output to the screen of the display device 160, and the user may identify the post-processed image in real time. According to various embodiments, the user may identify an image captured in real time and augmented biometric information while photography is performed through the camera and the finger is in contact with the sensor.

According to various embodiments, in the state shown in one of FIGS. 16B to 16E, when the finger contacting the sensor is removed from the sensor, biometric information measured up to that time point may be stored. According to various embodiments, in the state in one of FIGS. 16B to 16E, when a photography command is received, a user image may be captured and stored, and biometric information measured up to the photography time point may be stored along with meta information of the image. According to various embodiments, when the photography command is received, the electronic device 101 may capture and store a screen at the corresponding time point. According to various embodiments, when the finger contacting the sensor is removed from the sensor, the electronic device 101 may maintain the state in which an object related to health information is displayed up to the corresponding time point, or may not display the object on the screen according to configuration information of the electronic device 101.

According to various embodiments, when the user removes his/her finger from the sensor, the electronic device 101 may capture the post-processed image displayed on the screen and output a message querying the user about whether to store the image. According to an embodiment, when a storage request is received from the user, the electronic device 101 may store the post-processed image in the memory of the electronic device 101. According to various embodiments, the post-processed image may be stored in various forms according to, for example, an option predetermined by the user. For example, the option may include a function of storing the post-processed image, storing the original image, storing biometric information separately, or storing biometric information in an integrated manner. Additionally or alternatively, when there is external storage space preconfigured by the user, the electronic device 101 may transmit and store the post-processed image to the corresponding external storage space through direct (for example, wired) communication or wireless communication.

According to various embodiments, when there is no storage request from the user and contact between the sensor and finger is detected again, the electronic device 101 may enter the selfie mode again without storing the captured post-processed image, and may repeat the operation according to various embodiments before the end of input by the user.

FIG. 17 illustrates another example of an operation scenario in which the electronic device provides health information to the user according to various embodiments.

As illustrated in FIG. 17, FIG. 17 illustrates an example of an operation in which the electronic device 101 provides health information related to the user while a voice call mode is executed. According to an embodiment, the example of FIG. 17 corresponds to the operation in the part described with reference to FIG. 16, and may be an example of acquiring biometric information and displaying objects related to health information, estimated on the basis of the biometric information.

According to various embodiments, the electronic device 101 may enter the voice call mode and display an execution screen related to the voice call mode through the display device 160.

According to various embodiments, as illustrated in FIG. 7A, the user may bring his/her finger into contact with the sensor 710 disposed on the rear surface of the electronic device 101 while the voice call mode is being used. According to various embodiments, the electronic device 101 may monitor whether the user's finger contacts the sensor 710 while the voice call mode is executed. According to an embodiment, the electronic device 101 may enter a health mode in response to detection of contact with the sensor 710, and may continuously collect (or measure) the user's biometric information over time.

According to various embodiments, the electronic device 101 may provide the estimated health information to the user on the basis of a relevant object. According to an embodiment, the electronic device 101 may estimate at least one piece of health information on the basis of biometric information acquired (or accumulated) over time, and may additionally display estimated (or updated) health information, or may augment and display the conventional health information.

Figure 17A:
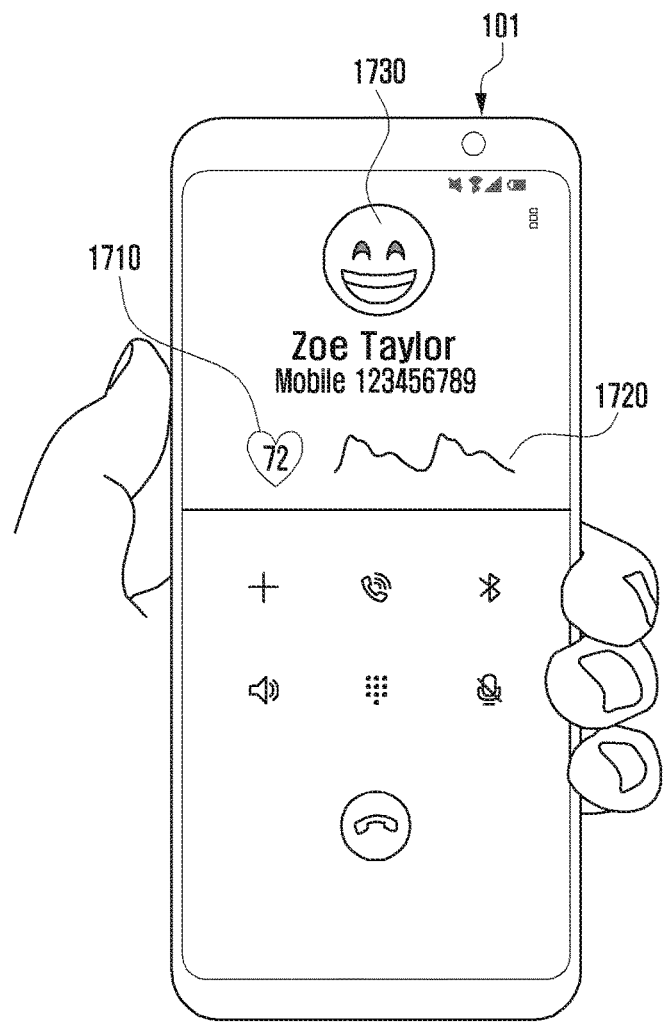
FIGS. 17A and 17B illustrate another example of the operation scenario in which the electronic device provides health information to the user according to various embodiments.

According to an embodiment, as illustrated in FIG. 17A, when contact between the sensor 710 and the finger is detected during a voice call with another electronic device (for example, a counterpart electronic device), the electronic device 101 may measure the user's biometric information. The electronic device 101 may estimate at least one piece of health information on the basis of the measurement time of the health information, and may display objects 1710, 1720, and 1730 corresponding to the estimated health information in selected areas.

According to various embodiments, provided health information (for example, emotion information, stress information, and heart-rate information) may be stored while being associated with (or mapped to) logs of calls (for example, phone call logs) with another electronic device or counterpart information (for example, a name, a nickname, or a phone number) registered in the contacts of the electronic device 101.

Figure 17B:
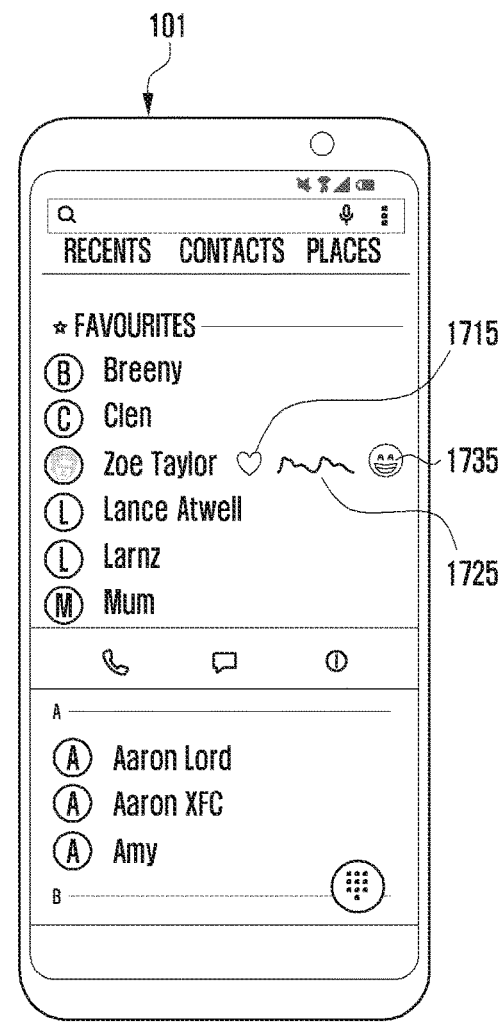

For example, as illustrated in FIG. 17B, the electronic device 101 may display health items 1715, 1725, and 1735 corresponding to the objects 1710, 1720, and 1730 of the health information to be associated with counterpart information (for example, Zoe Taylor) in the contacts. According to an embodiment, the health items 1715, 1725, and 1735 may be indicated in the form of text, icons, or waveforms, and may be provided in a form corresponding to the objects 1710, 1720, and 1730 of the health information estimated in FIG. 17A. According to an embodiment, the health items 1715, 1725, and 1735 may be provided as various shapes of items capable of intuitively indicating user's health information related to counterpart information, and may be provided in the form of one designated integrated icon for indicating the existence of health information. According to various embodiments, health information corresponding to the health items 1715, 1725, and 1735 may be stored for each call, and the health items 1715, 1725, and 1735 provided in FIG. 17B may correspond to health information estimated in the last call. Accordingly, the user may record and identify his/her own feeling at the time point at which a voice call with the counterpart is made.

According to an embodiment, user's voice information may be included in the voice call mode. According to various embodiments, the electronic device 101 may use user's voice information input in the voice call mode as data for measuring a user's emotional state, analyze biometric information and the voice information analysis result, and extract and provide more precise emotional state.

Figure 18:
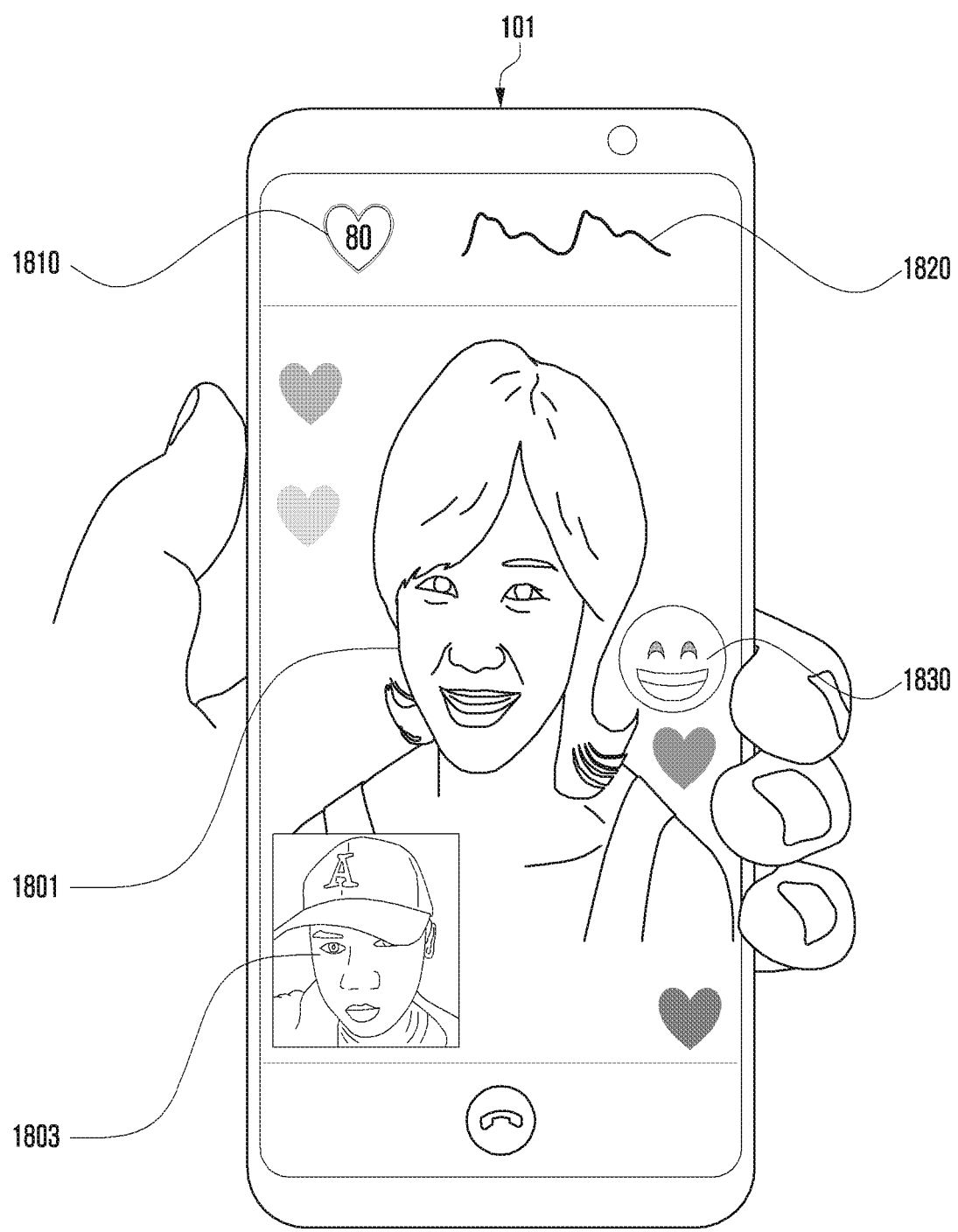
FIG. 18 illustrates another example of the operation scenario in which the electronic device provides health information to the user according to various embodiments.

FIG. 18 illustrates another example of the operation scenario in which the electronic device provides health information to the user according to various embodiments.

As illustrated in FIG. 18, FIG. 18 illustrates an example of an operation in which the electronic device 101 provides health information related to the user while a video call mode is executed. According to an embodiment, the example of FIG. 18 is an operation corresponding to the part described with reference to FIG. 16, and may be an example of acquiring biometric information and displaying objects related to health information estimated on the basis of the biometric information.

Referring to FIG. 18, the electronic device 101 may enter the video call mode and display an execution screen related to the video call mode through the display device 160. According to an embodiment, the execution screen related to the video call mode may include a first user image 1801 of the user, captured through the camera of the electronic device 101, and a second user image 1803 of a counterpart user, captured through a camera of another electronic device (for example, the electronic device of the counterpart). According to an embodiment, the first user image 1801 and the second user image 1802 may be provided through respective configured areas on the basis of at least a configuration related to the video call mode of the electronic device 101.

According to various embodiments, as illustrated in FIG. 7A, the user may bring his/her finger into contact with the sensor 710 disposed on the rear surface of the electronic device 101 while the video call mode is executed. According to various embodiments, the electronic device 101 may monitor whether the finger contacts the sensor 710 while the video call mode is executed. According to an embodiment, the electronic device 101 may enter a health mode in response to detection of contact with the sensor 710, and may continuously collect (or measure) user's biometric information over time.

According to various embodiments, the electronic device 101 may provide the estimated health information to the user on the basis of a relevant object. According to an embodiment, the electronic device 101 may estimate at least one piece of health information on the basis of biometric information acquired (or accumulated) over time, and may additionally display estimated (or updated) health information or augment and display the conventional health information.

According to an embodiment, as illustrated in FIG. 18, when contact between the sensor 710 and the finger is detected, the electronic device 101 may measure the user's biometric information while the video call mode with another electronic device (for example, a counterpart electronic device) is executed. The electronic device 101 may estimate at least one piece of health information on the basis of the measurement time of the health information, and may display objects 1810, 1820, and 1830 corresponding to the estimated health information in the selected area.

According to an embodiment, the user's voice information and image information may be included in the video call mode. According to various embodiments, the electronic device 101 may analyze the user's voice information and the image information input in the video call mode together with the biometric information and display a change in the user's emotion or stress, or a change in blood pressure with respect to the counterpart on the screen during the video call mode. According to an embodiment, when the change in user's health information (for example, emotion, stress, or blood pressure) is larger than or equal to a reference, the electronic device 101 may display a relevant object on the screen. According to various embodiments, the electronic device 101 may transmit user's health information to an electronic device participating therewith in a call, and may automatically display the user's health information on the other electronic device through at least a graphic effect or an avatar state.

According to various embodiments, health information (for example, emotion information, stress information, and heart-rate information) provided during the call with another electronic device may be stored while being associated with (mapped to) logs of calls with another electronic device or counterpart information (for example, a name, a nickname, or a phone number) registered in the contacts of the electronic device 101.

As described above, a method of operating the electronic device 101 according to various embodiments of the disclosure may include an operation of executing an application; acquiring first biometric information of a user through a sensor module 176 while an operation related to the application is performed, an operation of estimating health information of the user, based on at least the first biometric information, and an operation of associating the health information with the operation related to the application and displaying the health information through the display device 160.

According to various embodiments, the operation of acquiring the first biometric information of the user may include an operation of executing a health mode for performing an operation based on the first biometric information in the state in which the operation related to the application is maintained in response to detection of the first biometric information from the sensor module 176 while the operation related to the application is performed.

According to various embodiments, the operation of acquiring the first biometric information of the user may include an operation of determining whether there is previously measured second biometric information while the operation related to the application is performed in response to detection of the first biometric information from the sensor module 176.

According to various embodiments, the operation of acquiring the first biometric information of the user may include an operation of acquiring merged biometric information obtained by merging the previously measured biometric information and the first biometric information.

According to various embodiments, the first biometric information and the second biometric information may be discontinuous information measured in different contact sessions by the sensor module 176 while the operation related to the application is performed.

According to various embodiments, the operation of estimating the health information of the user may reduce an estimation time of the health information, based on the merged biometric information.

According to various embodiments, the operation of displaying the health information may include an operation of determining at least one piece of health information, based on the time required to measure the first biometric information and displaying a first object related to at least one piece of the health information in a configured area of the display device 160.

According to various embodiments, the operation of displaying the health information may include an operation of augmenting and displaying the first object displayed through the display device 160, based on the measurement time and an operation of displaying a second object related to the health information through the display device 160, based on the measurement time.

According to various embodiments, a first measurement time for acquiring the first object related to the health information may be shorter than a second measurement time for acquiring the second object related to the health information.

According to various embodiments, the operation of acquiring the first biometric information of the user may include an operation of acquiring additional third biometric information (for example, voice information and image information), based on a module (for example, the camera module 180 or the input device 150 (for example, a microphone)) related to the operation of the application while acquiring the first biometric information through the sensor module 176 so as to concurrently process the first biometric information and the third biometric information.

Various embodiments of the disclosure disclosed in the specifications and drawings present specific examples for ease of description of the technical content of the disclosure and to help understanding of the disclosure, but are not intended to limit the scope of the disclosure. Therefore, it should be construed that not only the embodiments disclosed herein but also all modifications or modified forms capable of being derived on the basis of the technical idea of the disclosure are included in the scope of the disclosure.

What is claimed is:

1. An electronic device comprising:
   a sensor;
   a camera;
   a display;
   at least one processor; and
   memory storing instructions that, when executed by the at least one processor, cause the electronic device to:
   execute an application,
   detect first biometric information of a user through the sensor while an operation related to the application is performed,
   determine whether second biometric information exists, previously measured and stored in the memory, while the operation related to the application is performed in response to detecting the first biometric information,
   when the first biometric information exists, acquire merged biometric information by merging the second biometric information and the first biometric information, estimate health information based on the merged biometric information, and display the health information in association with the executed application.

2. The electronic device of claim 1, wherein the instructions, when executed by the at least one processor, cause the electronic device to execute a health mode for performing an operation based on the first biometric information in a state in which the operation related to the application is maintained in response to detection of the first biometric information from the sensor while the operation related to the application is performed.

3. The electronic device of claim 1, wherein the first biometric information and the second biometric information are discontinuous information measured in different contact sessions by the sensor while the operation related to the application is performed.

4. The electronic device of claim 1, wherein the instructions, when executed by the at least one processor, cause the electronic device to reduce an estimation time of the health information, based on the merged biometric information.

5. The electronic device of claim 1, wherein the instructions, when executed by the at least one processor, cause the electronic device to:
   calculate a measurement time required for the first biometric information,
   determine at least one piece of health information that can be estimated based on the measurement time, and
   display a first object related to at least one piece of the health information in a configured area of the display.

6. The electronic device of claim 5, wherein the instructions, when executed by the at least one processor, cause the electronic device to:
   augment and display the first object, displayed through the display, based on the measurement time, and
   display a second object related to the health information through the display, based on the measurement time.

7. The electronic device of claim 6, wherein a first measurement time for acquiring the first object related to the health information is shorter than a second measurement time for acquiring the second object related to the health information.

8. The electronic device of claim 1, wherein the instructions, when executed by the at least one processor, cause the electronic device to acquire additional third biometric information, based on a device related to the operation of the application while acquiring the first biometric information through the sensor so as to concurrently process the first biometric information and the third biometric information.

9. A method of operating an electronic device, the method comprising:
executing an application;
detecting first biometric information of a user through a sensor while an operation related to the application is performed;
determining whether second biometric information exists, previously measured and stored in the memory, while the operation related to the application is performed in response to detecting the first biometric information;
when the first biometric information exists, acquiring merged biometric information by merging the second biometric information and the first biometric information;
estimating health information based on the merged biometric information; and
displaying the health information in association with the executed application.

10. The method of claim 9, wherein the acquiring of the first biometric information of the user comprises executing a health mode for performing an operation based on the first biometric information in a state in which the operation related to the application is maintained in response to detection of the first biometric information from the sensor while the operation related to the application is performed.

11. The method of claim 9,
wherein the first biometric information and the second biometric information are discontinuous information measured in different contact sessions by the sensor while the operation related to the application is performed.

12. The method of claim 9, wherein the estimating of the health information of the user comprises reducing an estimation time of the health information, based on the merged biometric information.

13. The method of claim 9, wherein the displaying of the health information comprises:
determining at least one piece of health information, based on a measurement time required for the first biometric information and displaying a first object related to at least one piece of the health information in a configured area of the display;
augmenting and displaying the first object, displayed through the display, based on the measurement time; and
displaying a second object related to the health information through the display, based on the measurement time.

14. The method of claim 9, wherein the acquiring of the first biometric information of the user comprises acquiring additional third biometric information, based on a device related to the operation related to the application while acquiring the first biometric information through the sensor so as to concurrently process the first biometric information and the third biometric information.

* * * * *